United States Patent
Rafii-Tari et al.

(10) Patent No.: US 11,058,493 B2
(45) Date of Patent: Jul. 13, 2021

(54) ROBOTIC SYSTEM CONFIGURED FOR NAVIGATION PATH TRACING

(71) Applicant: Auris Health, Inc., Redwood City, CA (US)

(72) Inventors: Hedyeh Rafii-Tari, Mountain View, CA (US); Prasanth Jeevan, San Mateo, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 16/143,362

(22) Filed: Sep. 26, 2018

(65) Prior Publication Data

US 2019/0110839 A1    Apr. 18, 2019

Related U.S. Application Data

(60) Provisional application No. 62/572,285, filed on Oct. 13, 2017.

(51) Int. Cl.
*A61B 34/10*     (2016.01)
*A61B 34/20*     (2016.01)
(Continued)

(52) U.S. Cl.
CPC .............. *A61B 34/10* (2016.02); *A61B 34/20* (2016.02); *A61B 34/37* (2016.02); *A61B 90/37* (2016.02);
(Continued)

(58) Field of Classification Search
None
See application file for complete search history.

(56) References Cited

U.S. PATENT DOCUMENTS

| 4,745,908 A | 5/1988 | Wardle |
| 5,273,025 A | 12/1993 | Sakiyam et al. |

(Continued)

FOREIGN PATENT DOCUMENTS

| CN | 101147676 | 3/2008 |
| CN | 101222882 | 7/2008 |

(Continued)

OTHER PUBLICATIONS

Ciuti et al., 2012, Intro-operative monocular 30 reconstruction for image-guided navigation in active locomotion capsule endoscopy. Biomedical Robotics and Biomechatronics (Biorob), 4th IEEE Ras & Embs International Conference on IEEE.

(Continued)

*Primary Examiner* — Katherine L Fernandez
(74) *Attorney, Agent, or Firm* — Chang & Hale LLP

(57) ABSTRACT

Certain aspects relate to systems and techniques for navigation path tracing. In one aspect, a system displays a preoperative model of a luminal network is displayed. The system determines a position of an instrument within the luminal network relative to the preoperative model. Based on the position of the instrument relative to the preoperative model, the system determines whether to enter a path tracing mode. In path tracing mode the system displays visual indicia indicative of a path of the instrument with respect to the displayed preoperative model. The visual indicia may be used to visual the navigation path of the instrument and/or to extend the preoperative model.

29 Claims, 27 Drawing Sheets

(51) Int. Cl.
*A61B 34/37* (2016.01)
*A61B 90/00* (2016.01)
*A61B 90/30* (2016.01)
*A61B 17/00* (2006.01)
*A61B 34/00* (2016.01)
*A61B 34/30* (2016.01)

(52) U.S. Cl.
CPC .............. *A61B 2017/00477* (2013.01); *A61B 2017/00809* (2013.01); *A61B 2034/105* (2016.02); *A61B 2034/107* (2016.02); *A61B 2034/2051* (2016.02); *A61B 2034/2059* (2016.02); *A61B 2034/2061* (2016.02); *A61B 2034/252* (2016.02); *A61B 2034/301* (2016.02); *A61B 2090/306* (2016.02); *A61B 2090/309* (2016.02); *A61B 2090/3614* (2016.02)

(56) References Cited

U.S. PATENT DOCUMENTS

| | | | |
|---|---|---|---|
| 5,526,812 A | 6/1996 | Dumoulin et al. |
| 5,550,953 A | 8/1996 | Seraji |
| 5,831,614 A | 11/1998 | Tognazzini et al. |
| 5,935,075 A | 8/1999 | Casscells |
| 6,038,467 A | 3/2000 | De Bliek et al. |
| 6,047,080 A | 4/2000 | Chen |
| 6,059,718 A | 5/2000 | Taniguchi et al. |
| 6,063,095 A | 5/2000 | Wang et al. |
| 6,167,292 A | 12/2000 | Badano |
| 6,203,493 B1 | 3/2001 | Ben-Haim |
| 6,246,784 B1 | 6/2001 | Summers |
| 6,246,898 B1 | 6/2001 | Vesely |
| 6,332,089 B1 | 12/2001 | Acker |
| 6,425,865 B1 | 7/2002 | Salcudean et al. |
| 6,466,198 B1 | 10/2002 | Feinstein |
| 6,490,467 B1 | 12/2002 | Bucholz |
| 6,553,251 B1 | 4/2003 | Landesmaki |
| 6,665,554 B1 | 12/2003 | Charles |
| 6,690,963 B2 | 2/2004 | Ben-Haim |
| 6,690,964 B2 | 2/2004 | Beiger et al. |
| 6,812,842 B2 | 11/2004 | Dimmer |
| 6,899,672 B2 | 5/2005 | Chin |
| 6,926,709 B2 | 8/2005 | Beiger et al. |
| 7,180,976 B2 | 2/2007 | Wink |
| 7,206,627 B2 | 4/2007 | Abovitz |
| 7,233,820 B2 | 6/2007 | Gilboa |
| 7,386,339 B2 | 6/2008 | Strommer et al. |
| 7,756,563 B2 | 7/2010 | Higgins |
| 7,850,642 B2 | 12/2010 | Moll et al. |
| 7,901,348 B2 | 3/2011 | Soper |
| 8,155,403 B2 | 4/2012 | Tschirren |
| 8,190,238 B2 | 5/2012 | Moll et al. |
| 8,298,135 B2 | 10/2012 | Ito et al. |
| 8,317,746 B2 | 11/2012 | Sewell et al. |
| 8,394,054 B2 | 3/2013 | Wallace et al. |
| 8,460,236 B2 | 6/2013 | Roelle et al. |
| 8,821,376 B2 | 9/2014 | Tolkowsky |
| 8,858,424 B2 | 10/2014 | Hasegawa |
| 8,929,631 B2 | 1/2015 | Pfister et al. |
| 9,014,851 B2 | 4/2015 | Wong et al. |
| 9,125,639 B2 | 9/2015 | Mathis |
| 9,138,129 B2 | 9/2015 | Diolaiti |
| 9,183,354 B2 | 11/2015 | Baker et al. |
| 9,186,046 B2 | 11/2015 | Ramamurthy et al. |
| 9,272,416 B2 | 3/2016 | Hourtash et al. |
| 9,289,578 B2 | 3/2016 | Walker et al. |
| 9,459,087 B2 | 10/2016 | Dunbar |
| 9,504,604 B2 | 11/2016 | Alvarez |
| 9,561,083 B2 | 2/2017 | Yu et al. |
| 9,603,668 B2 | 3/2017 | Weingarten et al. |
| 9,622,827 B2 | 4/2017 | Yu et al. |
| 9,629,682 B2 | 4/2017 | Wallace et al. |
| 9,636,184 B2 | 5/2017 | Lee et al. |
| 9,710,921 B2 | 7/2017 | Wong et al. |
| 9,713,509 B2 | 7/2017 | Schuh et al. |
| 9,717,563 B2 | 8/2017 | Tognaccini |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,818,681 B2 | 11/2017 | Machida |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,136,950 B2 | 11/2018 | Schoenefeld |
| 10,143,526 B2 | 12/2018 | Walker et al. |
| 10,145,747 B1 | 12/2018 | Lin et al. |
| 10,159,532 B1 | 12/2018 | Ummalaneni et al. |
| 10,278,778 B2 | 5/2019 | State |
| 10,299,870 B2 | 5/2019 | Connolly et al. |
| 10,524,866 B2 | 1/2020 | Srinivasan |
| 2001/0021843 A1 | 9/2001 | Bosselmann et al. |
| 2001/0039421 A1 | 11/2001 | Heilbrun |
| 2002/0065455 A1 | 5/2002 | Ben-Haim et al. |
| 2002/0077533 A1 | 6/2002 | Bieger et al. |
| 2002/0120188 A1 | 8/2002 | Brock et al. |
| 2003/0105603 A1 | 6/2003 | Hardesty |
| 2003/0125622 A1 | 7/2003 | Schweikard |
| 2003/0181809 A1 | 9/2003 | Hall et al. |
| 2003/0195664 A1 | 10/2003 | Nowlin et al. |
| 2004/0047044 A1 | 3/2004 | Dalton |
| 2004/0072066 A1 | 4/2004 | Cho et al. |
| 2004/0186349 A1 | 9/2004 | Ewers |
| 2004/0249267 A1* | 12/2004 | Gilboa ............... A61B 1/00154 600/424 |
| 2004/0263535 A1 | 12/2004 | Birkenbach et al. |
| 2005/0027397 A1 | 2/2005 | Niemeyer |
| 2005/0060006 A1 | 3/2005 | Pflueger |
| 2005/0085714 A1 | 4/2005 | Foley et al. |
| 2005/0107679 A1 | 5/2005 | Geiger |
| 2005/0143649 A1 | 6/2005 | Minai et al. |
| 2005/0143655 A1 | 6/2005 | Satoh |
| 2005/0182295 A1* | 8/2005 | Soper ................. A61B 1/00172 600/117 |
| 2005/0193451 A1 | 9/2005 | Quistgaard et al. |
| 2005/0256398 A1 | 11/2005 | Hastings |
| 2005/0272975 A1 | 12/2005 | McWeeney et al. |
| 2006/0004286 A1 | 1/2006 | Chang |
| 2006/0015096 A1 | 1/2006 | Hauck et al. |
| 2006/0025668 A1 | 2/2006 | Peterson |
| 2006/0058643 A1 | 3/2006 | Florent |
| 2006/0084860 A1* | 4/2006 | Geiger ................... A61B 10/04 600/407 |
| 2006/0095066 A1 | 5/2006 | Chang |
| 2006/0098851 A1 | 5/2006 | Shoham |
| 2006/0149134 A1 | 7/2006 | Soper et al. |
| 2006/0173290 A1 | 8/2006 | Lavallee et al. |
| 2006/0184016 A1 | 8/2006 | Glossop |
| 2006/0209019 A1 | 9/2006 | Hu |
| 2006/0258935 A1 | 11/2006 | Pile-Spellman et al. |
| 2006/0258938 A1 | 11/2006 | Hoffman et al. |
| 2007/0032826 A1 | 2/2007 | Schwartz |
| 2007/0055128 A1 | 3/2007 | Glossop |
| 2007/0055144 A1 | 3/2007 | Neustadter |
| 2007/0073136 A1 | 3/2007 | Metzger |
| 2007/0083193 A1 | 4/2007 | Werneth |
| 2007/0123748 A1 | 5/2007 | Meglan |
| 2007/0135886 A1 | 6/2007 | Maschke |
| 2007/0156019 A1 | 7/2007 | Larkin et al. |
| 2007/0167743 A1 | 7/2007 | Honda |

(56) References Cited

U.S. PATENT DOCUMENTS

| | | |
|---|---|---|
| 2007/0167801 A1 | 7/2007 | Webler et al. |
| 2007/0208252 A1 | 9/2007 | Makower |
| 2007/0253599 A1 | 11/2007 | White et al. |
| 2007/0269001 A1 | 11/2007 | Maschke |
| 2007/0293721 A1 | 12/2007 | Gilboa |
| 2007/0299353 A1 | 12/2007 | Harley et al. |
| 2008/0071140 A1 | 3/2008 | Gattani |
| 2008/0079421 A1 | 4/2008 | Jensen |
| 2008/0103389 A1 | 5/2008 | Begelman et al. |
| 2008/0118118 A1 | 5/2008 | Berger |
| 2008/0118135 A1 | 5/2008 | Averbach |
| 2008/0123921 A1 | 5/2008 | Gielen et al. |
| 2008/0147089 A1 | 6/2008 | Loh |
| 2008/0161681 A1 | 7/2008 | Hauck |
| 2008/0183064 A1 | 7/2008 | Chandonnet |
| 2008/0183068 A1 | 7/2008 | Carls et al. |
| 2008/0183073 A1* | 7/2008 | Higgins ................ G06T 19/003 600/425 |
| 2008/0183188 A1 | 7/2008 | Carls et al. |
| 2008/0201016 A1 | 8/2008 | Finlay |
| 2008/0207997 A1* | 8/2008 | Higgins ............. A61B 1/00009 600/114 |
| 2008/0212082 A1 | 9/2008 | Froggatt et al. |
| 2008/0218770 A1 | 9/2008 | Moll et al. |
| 2008/0243142 A1 | 10/2008 | Gildenberg |
| 2008/0262297 A1 | 10/2008 | Gilboa |
| 2008/0275349 A1 | 11/2008 | Halperin |
| 2008/0287963 A1 | 11/2008 | Rogers et al. |
| 2008/0306490 A1 | 12/2008 | Lakin et al. |
| 2008/0312501 A1 | 12/2008 | Hasegawa et al. |
| 2009/0030307 A1 | 1/2009 | Govari |
| 2009/0054729 A1 | 2/2009 | Mori |
| 2009/0076476 A1 | 3/2009 | Barbagli et al. |
| 2009/0149867 A1 | 6/2009 | Glozman |
| 2009/0227861 A1 | 9/2009 | Ganatra |
| 2009/0248036 A1 | 10/2009 | Hoffman et al. |
| 2009/0259230 A1 | 10/2009 | Khadem |
| 2009/0262109 A1 | 10/2009 | Markowitz et al. |
| 2009/0292166 A1 | 11/2009 | Ito |
| 2009/0295797 A1 | 12/2009 | Sakaguchi |
| 2010/0008555 A1 | 1/2010 | Trumer |
| 2010/0039506 A1 | 2/2010 | Sarvestani et al. |
| 2010/0041949 A1 | 2/2010 | Tolkowsky |
| 2010/0054536 A1 | 3/2010 | Huang |
| 2010/0113852 A1 | 5/2010 | Sydora |
| 2010/0121139 A1 | 5/2010 | OuYang |
| 2010/0160733 A1 | 6/2010 | Gilboa |
| 2010/0161022 A1 | 6/2010 | Tolkowsky |
| 2010/0161129 A1 | 6/2010 | Costa et al. |
| 2010/0225209 A1 | 9/2010 | Goldberg |
| 2010/0240989 A1 | 9/2010 | Stoianovici |
| 2010/0290530 A1 | 11/2010 | Huang et al. |
| 2010/0292565 A1 | 11/2010 | Meyer |
| 2010/0298641 A1 | 11/2010 | Tanaka |
| 2010/0328455 A1 | 12/2010 | Nam et al. |
| 2011/0054303 A1 | 3/2011 | Barrick |
| 2011/0092808 A1 | 4/2011 | Shachar |
| 2011/0184238 A1 | 7/2011 | Higgins |
| 2011/0234780 A1 | 9/2011 | Ito |
| 2011/0238082 A1 | 9/2011 | Wenderow |
| 2011/0245665 A1 | 10/2011 | Nentwick |
| 2011/0248987 A1 | 10/2011 | Mitchell |
| 2011/0249016 A1 | 10/2011 | Zhang |
| 2011/0276179 A1 | 11/2011 | Banks et al. |
| 2011/0319910 A1 | 12/2011 | Roelle et al. |
| 2012/0046521 A1 | 2/2012 | Hunter et al. |
| 2012/0056986 A1 | 3/2012 | Popovic |
| 2012/0062714 A1 | 3/2012 | Liu |
| 2012/0065481 A1 | 3/2012 | Hunter |
| 2012/0069167 A1 | 3/2012 | Liu et al. |
| 2012/0071782 A1 | 3/2012 | Patil et al. |
| 2012/0082351 A1 | 4/2012 | Higgins |
| 2012/0120305 A1 | 5/2012 | Takahashi |
| 2012/0165656 A1 | 6/2012 | Montag |
| 2012/0209069 A1 | 6/2012 | Popovic |
| 2012/0191079 A1 | 7/2012 | Moll et al. |
| 2012/0215094 A1 | 8/2012 | Rahimian et al. |
| 2012/0219185 A1 | 8/2012 | Hu |
| 2012/0289777 A1 | 11/2012 | Chopra |
| 2012/0289783 A1 | 11/2012 | Duindam et al. |
| 2012/0302869 A1 | 11/2012 | Koyrakh |
| 2013/0060146 A1 | 3/2013 | Yang et al. |
| 2013/0144116 A1 | 6/2013 | Cooper et al. |
| 2013/0165945 A9 | 6/2013 | Roelle |
| 2013/0204124 A1 | 8/2013 | Duindam |
| 2013/0225942 A1 | 8/2013 | Holsing |
| 2013/0243153 A1 | 9/2013 | Sra |
| 2013/0246334 A1 | 9/2013 | Ahuja |
| 2013/0259315 A1 | 10/2013 | Angot et al. |
| 2013/0303892 A1 | 11/2013 | Zhao |
| 2013/0345718 A1 | 12/2013 | Crawford |
| 2014/0058406 A1 | 2/2014 | Tsekos |
| 2014/0107390 A1 | 4/2014 | Brown |
| 2014/0114180 A1 | 4/2014 | Jain |
| 2014/0148608 A1 | 4/2014 | Inkpen et al. |
| 2014/0142591 A1 | 5/2014 | Alvarez et al. |
| 2014/0180063 A1 | 6/2014 | Zhao |
| 2014/0235943 A1 | 8/2014 | Paris |
| 2014/0243849 A1 | 8/2014 | Saglam |
| 2014/0257746 A1 | 9/2014 | Dunbar et al. |
| 2014/0264081 A1 | 9/2014 | Walker et al. |
| 2014/0275988 A1 | 9/2014 | Walker et al. |
| 2014/0276033 A1 | 9/2014 | Brannan |
| 2014/0276937 A1 | 9/2014 | Wong et al. |
| 2014/0296655 A1 | 10/2014 | Akhbardeh et al. |
| 2014/0309527 A1 | 10/2014 | Namati et al. |
| 2014/0309649 A1 | 10/2014 | Alvarez et al. |
| 2014/0343416 A1 | 11/2014 | Panescu |
| 2014/0350391 A1 | 11/2014 | Prisco et al. |
| 2014/0357953 A1 | 12/2014 | Roelle et al. |
| 2014/0357984 A1 | 12/2014 | Wallace et al. |
| 2014/0364670 A1 | 12/2014 | Alvarez et al. |
| 2014/0364739 A1 | 12/2014 | Liu |
| 2015/0051482 A1 | 2/2015 | Liu et al. |
| 2015/0051592 A1 | 2/2015 | Kintz |
| 2015/0054929 A1 | 2/2015 | Ito et al. |
| 2015/0057498 A1 | 2/2015 | Akimoto |
| 2015/0073266 A1 | 3/2015 | Brannan |
| 2015/0101442 A1 | 4/2015 | Romo |
| 2015/0119638 A1 | 4/2015 | Yu et al. |
| 2015/0141808 A1 | 5/2015 | Elhawary |
| 2015/0141858 A1 | 5/2015 | Razavi |
| 2015/0142013 A1 | 5/2015 | Tanner et al. |
| 2015/0164594 A1 | 6/2015 | Romo et al. |
| 2015/0164596 A1 | 6/2015 | Romo |
| 2015/0223725 A1 | 8/2015 | Engel |
| 2015/0223897 A1 | 8/2015 | Kostrzewski et al. |
| 2015/0223902 A1 | 8/2015 | Walker et al. |
| 2015/0255782 A1 | 9/2015 | Kim et al. |
| 2015/0265087 A1 | 9/2015 | Park |
| 2015/0265368 A1 | 9/2015 | Chopra |
| 2015/0275986 A1 | 10/2015 | Cooper |
| 2015/0287192 A1 | 10/2015 | Sasaki |
| 2015/0297133 A1 | 10/2015 | Jouanique-Dubuis et al. |
| 2015/0305650 A1 | 10/2015 | Hunter |
| 2015/0313503 A1 | 11/2015 | Seibel et al. |
| 2015/0335480 A1 | 11/2015 | Alvarez et al. |
| 2016/0000302 A1 | 1/2016 | Brown |
| 2016/0000414 A1 | 1/2016 | Brown |
| 2016/0000520 A1 | 1/2016 | Lachmanovich |
| 2016/0001038 A1 | 1/2016 | Rorno et al. |
| 2016/0008033 A1 | 1/2016 | Hawkins et al. |
| 2016/0111192 A1 | 4/2016 | Suzara |
| 2016/0128992 A1 | 5/2016 | Hudson |
| 2016/0183841 A1 | 6/2016 | Duindam et al. |
| 2016/0199134 A1 | 7/2016 | Brown et al. |
| 2016/0206389 A1 | 7/2016 | Miller |
| 2016/0213432 A1 | 7/2016 | Flexman |
| 2016/0228032 A1 | 8/2016 | Walker et al. |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0296294 A1 | 10/2016 | Moll et al. |
| 2016/0314710 A1 | 10/2016 | Jarc |

(56) References Cited

U.S. PATENT DOCUMENTS

| | | |
|---|---|---|
| 2016/0331469 A1 | 11/2016 | Hall et al. |
| 2016/0360947 A1 | 12/2016 | Iida |
| 2016/0372743 A1 | 12/2016 | Cho et al. |
| 2016/0374541 A1 | 12/2016 | Agrawal et al. |
| 2017/0007337 A1 | 1/2017 | Dan |
| 2017/0055851 A1 | 3/2017 | Al-Ali |
| 2017/0079725 A1 | 3/2017 | Hoffman |
| 2017/0079726 A1 | 3/2017 | Hoffman |
| 2017/0100199 A1 | 4/2017 | Yu et al. |
| 2017/0119413 A1 | 5/2017 | Romo |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0189118 A1 | 7/2017 | Chopra |
| 2017/0202627 A1 | 7/2017 | Sramek et al. |
| 2017/0209073 A1 | 7/2017 | Sramek et al. |
| 2017/0215808 A1 | 8/2017 | Shimol et al. |
| 2017/0215969 A1 | 8/2017 | Zhai et al. |
| 2017/0238807 A9 | 8/2017 | Veritkov et al. |
| 2017/0258366 A1 | 9/2017 | Tupin |
| 2017/0290631 A1 | 10/2017 | Lee et al. |
| 2017/0296032 A1 | 10/2017 | Li |
| 2017/0296202 A1 | 10/2017 | Brown |
| 2017/0325896 A1 | 11/2017 | Donhowe |
| 2017/0333679 A1 | 11/2017 | Jiang |
| 2017/0340241 A1 | 11/2017 | Yamada |
| 2017/0340396 A1 | 11/2017 | Romo et al. |
| 2017/0348067 A1 | 12/2017 | Krimsky |
| 2017/0360418 A1 | 12/2017 | Wong et al. |
| 2017/0360508 A1* | 12/2017 | Germain .............. A61B 34/10 |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0055582 A1* | 3/2018 | Krimsky .............. G16H 50/50 |
| 2018/0098690 A1 | 4/2018 | Iwaki |
| 2018/0177383 A1 | 6/2018 | Noonan et al. |
| 2018/0177556 A1 | 6/2018 | Noonan et al. |
| 2018/0177561 A1* | 6/2018 | Mintz .................. A61B 34/30 |
| 2018/0184988 A1 | 7/2018 | Walker et al. |
| 2018/0214011 A1 | 8/2018 | Graetzel et al. |
| 2018/0217734 A1 | 8/2018 | Koenig et al. |
| 2018/0221038 A1 | 8/2018 | Noonan et al. |
| 2018/0221039 A1 | 8/2018 | Shah |
| 2018/0240237 A1* | 8/2018 | Donhowe ............ A61B 1/0016 |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0286108 A1 | 10/2018 | Hirakawa |
| 2018/0289243 A1 | 10/2018 | Landey et al. |
| 2018/0289431 A1 | 10/2018 | Draper et al. |
| 2018/0308247 A1 | 10/2018 | Gupta |
| 2018/0325499 A1 | 11/2018 | Landey et al. |
| 2018/0333044 A1 | 11/2018 | Jenkins |
| 2018/0360435 A1 | 12/2018 | Romo |
| 2018/0368920 A1 | 12/2018 | Ummalaneni |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000576 A1 | 1/2019 | Mintz et al. |
| 2019/0046814 A1 | 2/2019 | Senden et al. |
| 2019/0066314 A1 | 2/2019 | Abhari |
| 2019/0083183 A1 | 3/2019 | Moll et al. |
| 2019/0086349 A1 | 3/2019 | Nelson |
| 2019/0105776 A1 | 4/2019 | Ho et al. |
| 2019/0105785 A1 | 4/2019 | Meyer |
| 2019/0107454 A1 | 4/2019 | Lin |
| 2019/0110843 A1 | 4/2019 | Ummalaneni et al. |
| 2019/0117176 A1 | 4/2019 | Walker et al. |
| 2019/0117203 A1 | 4/2019 | Wong et al. |
| 2019/0151148 A1 | 4/2019 | Alvarez et al. |
| 2019/0228528 A1 | 4/2019 | Mintz et al. |
| 2019/0125164 A1 | 5/2019 | Roelle et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0287673 A1 | 9/2019 | Michihata |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0039086 A1 | 2/2020 | Meyer |
| 2020/0046434 A1 | 2/2020 | Graetzel |
| 2020/0054405 A1 | 2/2020 | Schuh |
| 2020/0054408 A1 | 2/2020 | Schuh et al. |
| 2020/0060516 A1 | 2/2020 | Baez |
| 2020/0078103 A1 | 3/2020 | Duindam |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0155084 A1 | 5/2020 | Walker |
| 2020/0170630 A1 | 6/2020 | Wong |
| 2020/0170720 A1 | 6/2020 | Ummalaneni |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |

FOREIGN PATENT DOCUMENTS

| | | |
|---|---|---|
| CN | 102316817 | 1/2012 |
| CN | 102458295 | 5/2012 |
| CN | 102973317 | 3/2013 |
| CN | 103735313 | 4/2014 |
| CN | 105559850 | 5/2016 |
| CN | 105559886 | 5/2016 |
| CN | 105611881 | 5/2016 |
| CN | 106821498 | 6/2017 |
| CN | 104931059 | 9/2018 |
| EP | 3 025 630 | 6/2016 |
| KR | 10-2014-0009359 | 1/2014 |
| RU | 2569699 C2 | 11/2015 |
| WO | WO 05/087128 | 9/2005 |
| WO | WO 09/097461 | 6/2007 |
| WO | WO 15/089013 | 6/2015 |
| WO | WO 17/048194 | 3/2017 |

(56) References Cited

FOREIGN PATENT DOCUMENTS

| WO | WO 17/066108 | 4/2017 |
|----|--------------|--------|
| WO | WO 17/167754 | 10/2017 |

OTHER PUBLICATIONS

Fallavollita et al., 2010, Acquiring multiview C-arm images to assist cardiac ablation procedures, EURASIP Journal on Image and Video Processing, vol. 2010, Article ID 871408, pp. 1-10.
Haigron et al., 2004, Depth-map-based scene analysis for activew navigation in virtual angioscopy, IEEE Transactions on Medical Imaging, 23(11):1380-1390.
Kumar et al., 2014, Stereoscopic visualization of laparoscope image using depth information from 3D model, Computer methods and programs in biomedicine 113(3):862-868.
Livatino et al., 2015, Stereoscopic visualization and 3-D technologies in medical endoscopic teleoperation, IEEE.
Luo et al., 2010, Modified hybrid bronchoscope tracking based on sequential monte carlo sampler: Dynamic phantom validation, Asian Conference on Computer Vision. Springer, Berlin, Heidelberg.
Mourgues et al., 2002, Flexible calibration of actuated stereoscopic endoscope for overlay inrobot assisted surgery, International Conference on Medical Image Computing and Computer-Assisted Intervention. Springer, Berlin, Heidelberg.
Nadeem et al., 2016, Depth Reconstruction and Computer-Aided Polyp Detection in Optical Colonoscopy Video Frames, arXiv preprint arXiv:1609.01329.
Point Cloud, Sep. 10, 2010, Wikipedia, 2 pp.
Racadio et al., Dec. 2007, Live 3D guidance in the interventional radiology suite; AJR, 189:W357-W364.
Sato et al., 2016, Techniques of stapler-based navigational thoracoscopic segmentectomy using virtual assisted lung mapping (VAL-MAP), Journal of Thoracic Disease, 8(Suppl 9):S716.
Shen et al., 2015, Robust camera localisation with depth reconstruction for bronchoscopic navigation. International Journal of Computer Assisted Radiology and Surgery, 10(6):801-813.
Solheim et al., May 14, 2009, Navigated resection of giant intracranial meningiomas based on intraoperative 3D ultrasound, Acta Neurochir, 151:1143-1151.
Song et al., 2012, Autonomous and stable tracking of endoscope instrument tools with monocular camera, Advanced Intelligent Mechatronics (AIM), 2012 IEEE-ASME International Conference on. IEEE.
Verdaasdonk et al., Jan. 23, 2012, Effect of microsecond pulse length and tip shape on explosive bubble formation of 2.78 µm Er,Cr;YSGG and 2.94 µm Er:YAG laser, Proceedings of SPIE, vol. 8221, 12.
Yip et al., 2012, Tissue tracking and registration for image-guided surgery, IEEE transactions on medical imaging 31(11):2169-2182.
Zhou et al., 2010, Synthesis of stereoscopic views from monocular endoscopic videos, Computer Vision and Pattern Recognition Workshops (CVPRW), 2010 IEEE Computer Society Conference on IEEE.
Konen et al., 1998, The VN-project: endoscopic image processing for neurosurgery, Computer Aided Surgery, 3:1-6.
Mayo Clinic, Robotic Surgery, https://www.mayoclinic.org/tests-procedures/robotic-surgery/about/pac-20394974?p=1, downloaded from the internet on Jul. 12, 2018, 2 pp.
Shi et al., Sep. 14-18, 2014, Simultaneous catheter and environment modeling for trans-catheter aortic valve implantation, IEEE/RSJ International Conference on Intelligent Robots and Systems, pp. 2024-2029.
Vemuri et al., Dec. 2015, Inter-operative biopsy site relocations in endoluminal surgery, IEEE Transactions on Biomedical Engineering, Institute of Electrical and Electronics Engineers, <10.1109/TBME.2015.2503981>. <hal-01230752>.
Wilson et al., 2008, a buyer's guide to electromagnetic tracking systems for clinical applications, Proc. of SPCI, 6918:69182B-1 p. 6918B-11.
International Search Report and Written Opinion dated Nov. 21, 2018 in application No. PCT/US18/53206.
Al-Ahmad et al., dated 2005, Early experience with a computerized robotically controlled catheter system, Journal of Interventional Cardiac Electrophysiology, 12:199-202.
Gutierrez et al., Mar. 2008, A practical global distortion correction method for an image intensifier based x-ray fluoroscopy system, Med. Phys, 35(3):997-1007.
Hansen Medical, Inc. 2005, System Overview, product brochure, 2 pp., dated as available at http://hansenmedical.com/system.aspx on Jul. 14, 2006 (accessed Jun. 25, 2019 using the internet archive way back machine).
Hansen Medical, Inc. Bibliography, product brochure, 1 p., dated as available at http://hansenmedical.com/bibliography.aspx on Jul. 14, 2006 (accessed Jun. 25, 2019 using the internet archive way back machine).
Hansen Medical, Inc. dated 2007, Introducing the Sensei Robotic Catheter System, product brochure, 10 pp.
Hansen Medical, Inc. dated 2009, Sensei X Robotic Catheter System, product brochure, 5 pp.
Hansen Medical, Inc. Technology Advantages, product brochure, 1 p., dated as available at http://hansenmedical.com/advantages.aspx on Jul. 13, 2006 (accessed Jun. 25, 2019 using the internet archive way back machine).
Kiraly et al, 2002, Three-dimensional Human Airway Segmentation Methods for Clinical Virtual Bronchoscopy, Acad Radiol, 9:1153-1168.
Kiraly et al., Sep. 2004, Three-dimensional path planning for virtual bronchoscopy, IEEE Transactions on Medical Imaging, 23(9):1365-1379.
Marrouche et al., dated May 6, 2005, AB32-1, Preliminary human experience using a novel robotic catheter remote control, Heart Rhythm, 2(5):S63.
Oh et al., dated May 2005, P5-75, Novel robotic catheter remote control system: safety and accuracy in delivering RF Lesions in all 4 cardiac chambers, Heart Rhythm, 2(5):S277-S278.
Reddy et al., May 2005, P1-53. Porcine pulmonary vein ablation using a novel robotic catheter control system and real-time integration of CT imaging with electroanatomical mapping, Hearth Rhythm, 2(5):S121.
Slepian, dated 2010, Robotic Catheter Intervention: the Hansen Medical Sensei Robot Catheter System, PowerPoint presentation, 28 pp.
Solomon et al., Dec. 2000, Three-dimensional CT-Guided Bronchoscopy With a Real-Time Electromagnetic Position Sensor A Comparison of Two Image Registration Methods, Chest, 118(6):1783-1787.
EP Search report for appl No. 18866272, dated May, 3, 2021, 2 pages.
EP Search Report Opinion for appl No. 18866272, dated May 3, 2021, 7 pages.

* cited by examiner

ROBOTIC SYSTEM CONFIGURED FOR NAVIGATION PATH TRACING

CROSS-REFERENCE TO RELATED APPLICATION

This application claims the benefit of U.S. Provisional Application No. 62/572,285, filed Oct. 13, 2017, which is hereby incorporated by reference in its entirety.

TECHNICAL FIELD

This disclosure relates generally to systems and methods for navigation of medical instruments, and more particularly to navigation path tracing methods and navigation systems for medical instruments.

BACKGROUND

Medical procedures such as endoscopy (e.g., bronchoscopy) may involve accessing and visualizing the inside of a patient's lumen (e.g., airways) for diagnostic and/or therapeutic purposes. During a procedure, a flexible tubular tool or instrument, such as an endoscope, may be inserted into the patient's body. In some instances a second instrument can be passed through the endoscope to a tissue site identified for diagnosis and/or treatment.

Bronchoscopy is a medical procedure that allows a physician to examine the inside conditions of airways in a patient's lungs, such as bronchi and bronchioles. During the medical procedure, a thin, flexible tubular tool or instrument, known as a bronchoscope, may be inserted into the patient's mouth and passed down the patient's throat into his or her lung airways towards a tissue site identified for subsequent diagnosis and treatment. The bronchoscope can have an interior lumen (a "working channel") providing a pathway to the tissue site, and catheters and various medical tools can be inserted through the working channel to the tissue site.

In certain medical procedures, medical robotic systems may be used to control the insertion and/or manipulation of the medical instruments. Medical robotic system may include at least one robotic arm or other instrument positioning device including a manipulator assembly used to control the positioning of the medical instrument during the procedures.

SUMMARY

Robotically-enabled medical systems can be used to perform a variety of medical procedures, including both minimally invasive procedures, such as laparoscopic procedures, and non-invasive procedures, such as endoscopic procedures. Among endoscopic procedures, robotically-enabled medical systems can be used to perform bronchoscopy, ureteroscopy, gastroenterology, etc. During such procedures, a physician and/or computer system can navigate a medical instrument through a luminal network of a patient. The luminal network can include a plurality of branched lumens (such as in bronchial or renal networks), or a single lumen (such as a gastrointestinal tract). The robotically-enabled medical systems can include navigation systems for guiding (or assisting with the guidance of) the medical instrument through the luminal network. The navigation systems may provide guidance based at least in part on a preoperative model of the luminal network.

The preoperative model may be limited to only certain portions of the luminal network. That is, the luminal network may extend beyond the portions represented by the preoperative model. During a procedure, however, the physician may desire to navigate the medical instrument into portions of the luminal network not represented in the preoperative model. This can be difficult as the guidance provided by the navigation system can be based at least in part on the preoperative model. Further, when navigation a medical instrument beyond the preoperative model it is difficult for the physician to track the position of the instrument. In certain instances, a physician may not be able to navigate the medical instrument beyond the preoperative model, or, if the medical instrument is navigated beyond the preoperative model, it may be difficult to determine the position of the medical instrument.

The aforementioned issues, among others, are addressed by the luminal network navigation systems and techniques described herein. In some implementations, the disclosed techniques provide navigation path tracing. Navigation path tracing can provide a historical path (e.g., breadcrumbs) that illustrates the position (and past positions) of the medical instrument. The historical path can be displayed to the physician such that the physician can visualize portions of the luminal network that are not represented by the preoperative model. Navigation path tracing can be provided in the portions of the luminal network beyond the preoperative model. In some instances, navigation path tracing can be used to extend the preoperative model. In some instances, navigation path tracing can also be used within the portions of the luminal network represented by the preoperative model.

The systems, methods and devices of this disclosure each have several innovative aspects, no single one of which is solely responsible for the desirable attributes disclosed herein.

Accordingly, one aspect relates to a non-transitory computer readable storage medium having stored thereon instructions that, when executed, cause a processor of a device to at least: display, on a user display, a preoperative model corresponding to a mapped portion of a luminal network of a patient; determine a position of a distal end of an instrument that is positioned within the luminal network relative to the mapped portion of the preoperative model; based on the position of the distal end of the instrument relative to the mapped portion of the luminal network, enter a path tracing mode; when in the path tracing mode, display, on the user display, visual indicia indicative of a path of the distal end of the instrument with respect to the displayed preoperative model.

The first aspect may include one or more of the following features, in any combination: (a) wherein the instructions are configured to cause the processor of the device to enter the path tracing mode when the position of the distal end of the instrument is outside the mapped portion of the preoperative model; (b) wherein the instructions are configured to cause the processor of the device to deactivate the path tracing mode when the position of the distal end of the instrument is inside the mapped portion of the preoperative model; (c) wherein the instructions are configured to cause the processor of the device to enter the path tracing mode when the position of the distal end of the instrument is within 25%, 20%, 15%, 10%, or 5% an end of a last segment of the preoperative model; (d) wherein the visual indicia are indicative of historical positions of the distal end of the instrument within the luminal network; (e) wherein, in in path tracing mode, the instructions are configured to cause the processor of the device to adjust a frequency of the visual indicia based on a distance traveled by the instrument between the visual indicia; (f) wherein, in in path tracing mode, the instructions are configured to cause the processor of the device to adjust a frequency of the visual indicia based on a time elapsed between the visual indicia; (g) wherein the instructions are configured to cause the processor of the device to determine the position of the distal end of the instrument based on a plurality of navigation modalities when the instrument is positioned within the mapped portion of the preoperative model; (h) wherein the plurality of navigation modalities comprise a plurality of preoperative model data, vision data, position sensor data, shape sensing data, and/or robotic command and kinematics data (i) wherein the instructions are configured to cause the processor of the device to determine the position of the distal end of the instrument based on less than the plurality of navigation modalities when the instrument is positioned outside the mapped portion of the preoperative model; (j) wherein the instructions are configured to cause the processor of the device to determine the position of the distal end of the instrument based EM data received from an EM sensor when the instrument is positioned outside the mapped portion of the preoperative model; (k) wherein the instructions are configured to cause the processor of the device to determine the position of the distal end of the instrument based on a combination of vision data and robotic command and kinematics data when the instrument is positioned outside the mapped portion of the preoperative model; (l) wherein the instructions are configured to cause the processor of the device to associate vision data with the visual indicia; (m) wherein the vision data comprises an image received from an imaging device on the distal end of the instrument; (n) wherein the instructions are configured to cause the processor of the device to associate robotic command and kinematics data with the visual indicia; and/or (o) wherein the instructions are configured to cause the processor of the device to: receive user input data from a user input; and associate the user input data with the visual indicia; (p) wherein the user input data comprises one or more of: an indication of a lumen traveled; an indication of a lumen not traveled; an indication of an end of a lumen; an indication of an opening of a lumen; and an indication that a current lumen extends beyond a current position of the instrument; and a lumen diameter; (q) wherein the instructions are configured to cause the processor of the device to fit geometric structures to the visual indicia to provide a visualization of a lumen of the luminal network outside of the mapped portion of the luminal network; (r) wherein the luminal network comprises a branched network of lumens; and/or (s) wherein the luminal network comprises a single lumen.

A second aspect relates to a robotic surgical or medical system for navigating a luminal network, the system comprising: an instrument having an elongate body and a sensor disposed on a distal end of the elongate body; at least one computer-readable memory having stored thereon executable instructions; and one or more processors in communication with the at least one computer-readable memory and configured to execute the instructions to cause the system to at least: access a preoperative model of a mapped portion of the luminal network and display the preoperative model on a user display; determine a position of the distal end of the instrument within the luminal network relative to the preoperative model using the sensor; detect, based on the determined position relative to the preoperative model, when the distal end of the instrument has moved beyond the mapped portion of the luminal network; and when the distal end of the instrument has moved beyond the mapped portion of the luminal network, display visual indicia of the position of the distal end of the instrument with respect to the displayed preoperative model on the user display.

The second aspect may include one or more of the following features, in any combination: (a) wherein the one or more processors are configured to execute the instructions to cause the system to register a coordinate frame of the sensor and a coordinate frame of the preoperative model; (b) a field generator configured to generate an EM field, wherein the sensor is an EM sensor, and wherein the one or more processors are configured to execute the instructions to cause the system determine a position of the EM sensor within the EM field; (c) wherein the sensor is a shape sensing fiber; (d) wherein the one or more processors are configured to execute the instructions to cause the system to move the instrument within the luminal network; (e) wherein the one or more processors are configured to execute the instructions to cause the system to at least: detect when the position of the distal end of the instrument is moved into the mapped portion of the luminal network; and stop displaying the visual indicia when the distal end of the instrument is positioned inside the mapped portion of the luminal network; (f) wherein the visual indicia are indicative of historical positions of the distal end of the instrument within the luminal network; (g) wherein the instructions are configured to cause the one or more processors to adjust a frequency of the visual indicia based on a distance traveled by the instrument between the visual indicia; (h) wherein the instructions are configured to cause the one or more processors to adjust a frequency of the visual indicia based on a time elapsed between the visual indicia; (i) wherein the instructions are configured to cause the one or more processors to determine the position of the distal end of the instrument based on a plurality of navigation modalities when the instrument is positioned within the mapped portion of the preoperative model; (j) wherein the plurality of navigation modalities comprise a plurality of preoperative model data, vision data, position sensor data, shape sensing data, and/or robotic command and kinematics data; (k) wherein the instructions are configured to cause the processor of the device to determine the position of the distal end of the instrument based on less than the plurality of navigation modalities when the instrument is positioned outside the mapped portion of the preoperative model; (l) wherein the instructions are configured to cause the one or more processors to determine the position of the distal end of the instrument based on a combination of vision data and robotic command and kinematics data when the instrument is positioned outside the mapped portion of the preoperative model; (m) wherein the instructions are configured to cause the one or more processors to associate vision data with the visual indicia; (n) wherein the vision data comprises an image received from an imaging device on the distal end of the instrument; (o) wherein the instructions are configured to cause the one or more processors to associate robotic command and kinematics data with the visual indicia; (p) wherein the instructions are configured to cause the one or more processors to: receive user input data from a user input; and associate the user input data with the visual indicia; (q) wherein the user input data comprises one or more of: an indication of a lumen traveled; an indication of a lumen not traveled; an indication of an end of a lumen; an indication of an opening of a lumen; an indication that a current lumen extends beyond a current position of the instrument; and a lumen diameter; (r) wherein the instructions are configured to cause the one or more processors to fit geometric structures to the visual indicia to provide a visualization of a lumen of the luminal network outside of the mapped portion of the luminal network; (s) wherein the luminal network comprises a branched network of lumens; (t) wherein the luminal network comprises a single lumen; (u) wherein the instrument is an endoscope; (v) an instrument positioning device, wherein the instrument is attached to the instrument positioning device; and/or (w) wherein the instrument positioning device comprises a robotic arm.

A third aspect relates to a method of determining a navigation path of an instrument within a luminal network, the method comprising: displaying, on a user interface, a preoperative model corresponding to a mapped portion of a luminal network; determining a position of a distal end of an instrument within the luminal network relative to the mapped portion of the luminal network; moving the instrument within the luminal network; determining when the distal end of the instrument has been advanced past the mapped portion of the luminal network into an unmapped portion of the luminal network and entering a path tracing mode; and when in the path tracing mode, displaying visual indicia of a path of the distal end of the instrument in the unmapped portion of the luminal network relative to the preoperative model of the mapped portion of the luminal network.

The third aspect may include one or more of the following features, in any combination: (a) detecting when the position of the distal end of the instrument is moved into the mapped portion of the luminal network; and stopping displaying the visual indicia when the distal end of the instrument is positioned inside the mapped portion of the luminal network; (b) wherein the visual indicia are indicative of historical positions of the distal end of the instrument within the luminal network; (c) adjusting a frequency of the visual indicia based on a distance traveled by the instrument between the visual indicia; (d) adjusting a frequency of the visual indicia based on a time elapsed between the visual indicia; (e) wherein determining the position of the distal end of the instrument is based on a plurality of navigation modalities when the instrument is positioned within the mapped portion of the preoperative model; (f) wherein the plurality of navigation modalities comprise a plurality of preoperative model data, vision data, position sensor data, shape sensing data, and/or robotic command and kinematics data; (g) wherein determining the position of the distal end of the instrument is based on less than the plurality of navigation modalities when the instrument is positioned outside the mapped portion of the preoperative model; (h) wherein determining the position of the distal end of the instrument is based EM data received from an EM sensor when the instrument is positioned outside the mapped portion of the preoperative model; (i) wherein determining the position of the distal end of the instrument is based on a combination of vision data and robotic command and kinematics data when the instrument is positioned outside the mapped portion of the preoperative model; (j) associating vision data with the visual indicia; (k) wherein the vision data comprises an image received from an imaging device on the distal end of the instrument; (l) associating robotic command and kinematics data with the visual indicia; (m) receiving user input data from a user input; and associating the user input data with the visual indicia; (n) wherein the user input data comprises one or more of: an indication of a lumen traveled; an indication of a lumen not traveled; an indication of an end of a lumen; an indication of an opening of a lumen; an indication that a current lumen extends beyond a current position of the instrument; and a lumen diameter; (o) fitting geometric structures to the visual indicia to provide a visualization of a lumen of the luminal network outside of the mapped portion of the luminal network; (p) wherein the luminal network comprises a branched network of lumens; and/or (q) wherein the luminal network comprises a single lumen.

A fourth aspect relates to a non-transitory computer readable storage medium having stored thereon instructions that, when executed, cause a processor of a device to at least: display, on a user display, a preoperative model corresponding to a mapped portion of a luminal network of a patient; determine a position of a distal end of an instrument that is positioned within the luminal network relative to the preoperative model; detect when the position of the distal end of the instrument is moved beyond the mapped portion of the luminal network; and display, on the user display, visual indicia indicative of the position of the distal end of the instrument with respect to the displayed preoperative model when the distal end of the instrument is positioned outside the mapped portion of the luminal network.

The fourth aspect may include one or more of the following features, in any combination: (a) wherein the instructions are configured to cause the processor of the device to: detect when the position of the distal end of the instrument is moved into the mapped portion of the luminal network; and stop displaying the visual indicia when the distal end of the instrument is positioned inside the mapped portion of the luminal network; (b) wherein the visual indicia are indicative of historical positions of the distal end of the instrument within the luminal network; (c) wherein the instructions are configured to cause the processor of the device to adjust a frequency of the visual indicia based on a distance traveled by the instrument between the visual indicia; (d) wherein the instructions are configured to cause the processor of the device to adjust a frequency of the visual indicia based on a time elapsed between the visual indicia; (e) wherein the instructions are configured to cause the processor of the device to determine the position of the distal end of the instrument based on a plurality of navigation modalities when the instrument is positioned within the mapped portion of the preoperative model; (f) wherein the plurality of navigation modalities comprise a plurality of preoperative model data, vision data, position sensor data, shape sensing data, and/or robotic command and kinematics data; (g) wherein the instructions are configured to cause the processor of the device to determine the position of the distal end of the instrument based on less than the plurality of navigation modalities when the instrument is positioned outside the mapped portion of the preoperative model; (h) wherein the instructions are configured to cause the processor of the device to determine the position of the distal end of the instrument based EM data received from an EM sensor when the instrument is positioned outside the mapped portion of the preoperative model; (i) wherein the instructions are configured to cause the processor of the device to determine the position of the distal end of the instrument based on a combination of vision data and robotic command and kinematics data when the instrument is positioned outside the mapped portion of the preoperative model; (j) wherein the instructions are configured to cause the processor of the device to associate vision data with the visual indicia; (k) wherein the vision data comprises an image received from an imaging device on the distal end of the instrument; (l) wherein the instructions are configured to cause the processor of the device to associate robotic command and kinematics data with the visual indicia; (m)

wherein the instructions are configured to cause the processor of the device to: receive user input data from a user input; and associate the user input data with the visual indicia; (n) wherein the user input data comprises one or more of: an indication of a lumen traveled; an indication of a lumen not traveled; an indication of an end of a lumen; an indication of an opening of a lumen; and an indication that a current lumen extends beyond a current position of the instrument; and a lumen diameter; (p) wherein the instructions are configured to cause the processor of the device to fit geometric structures to the visual indicia to provide a visualization of a lumen of the luminal network outside of the mapped portion of the luminal network; (q) wherein the luminal network comprises a branched network of lumens; and/or (r) wherein the luminal network comprises a single lumen.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
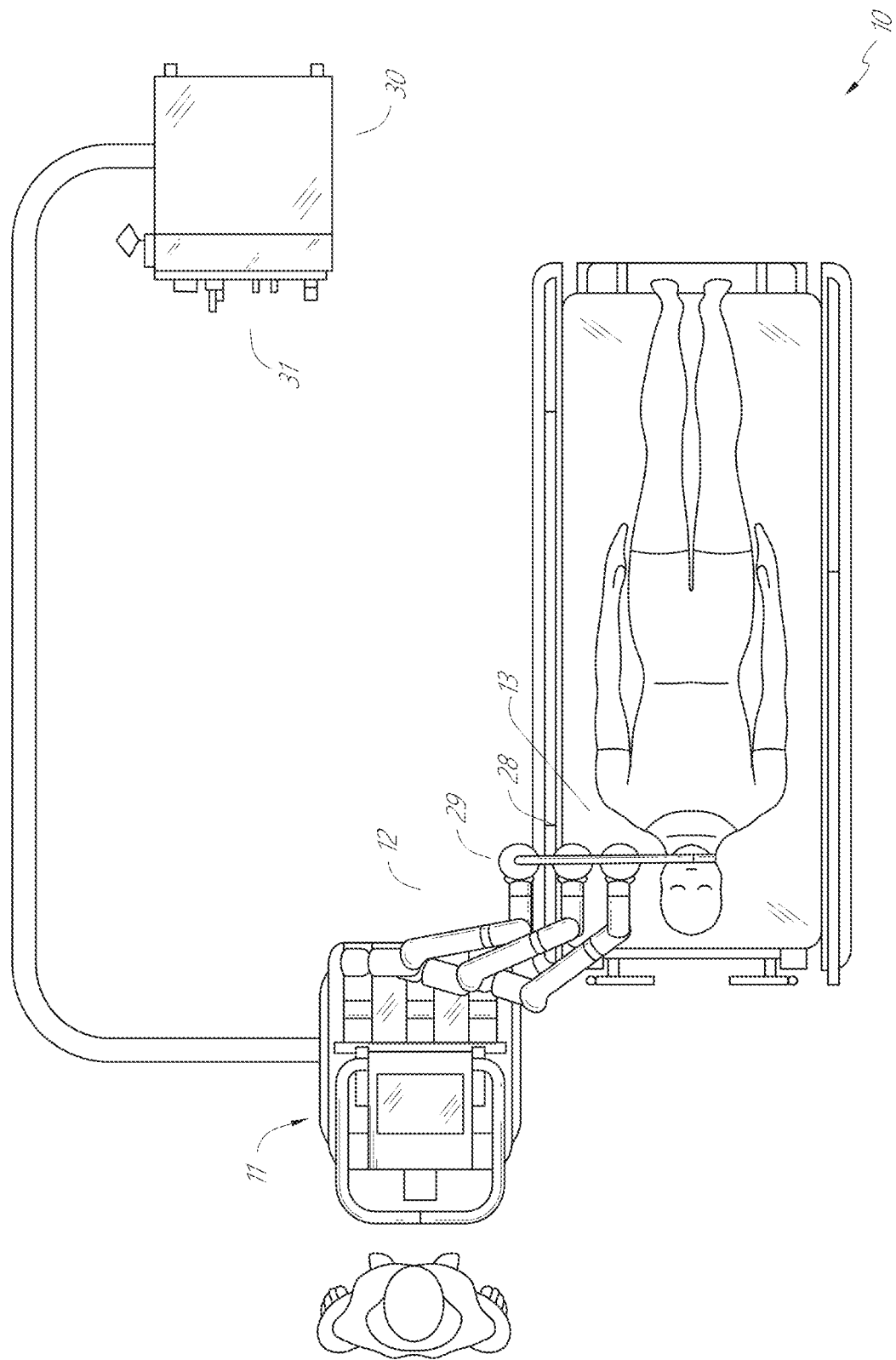
FIG. 1 illustrates an embodiment of a cart-based robotic system arranged for diagnostic and/or therapeutic bronchoscopy procedure(s).
Figure 2:
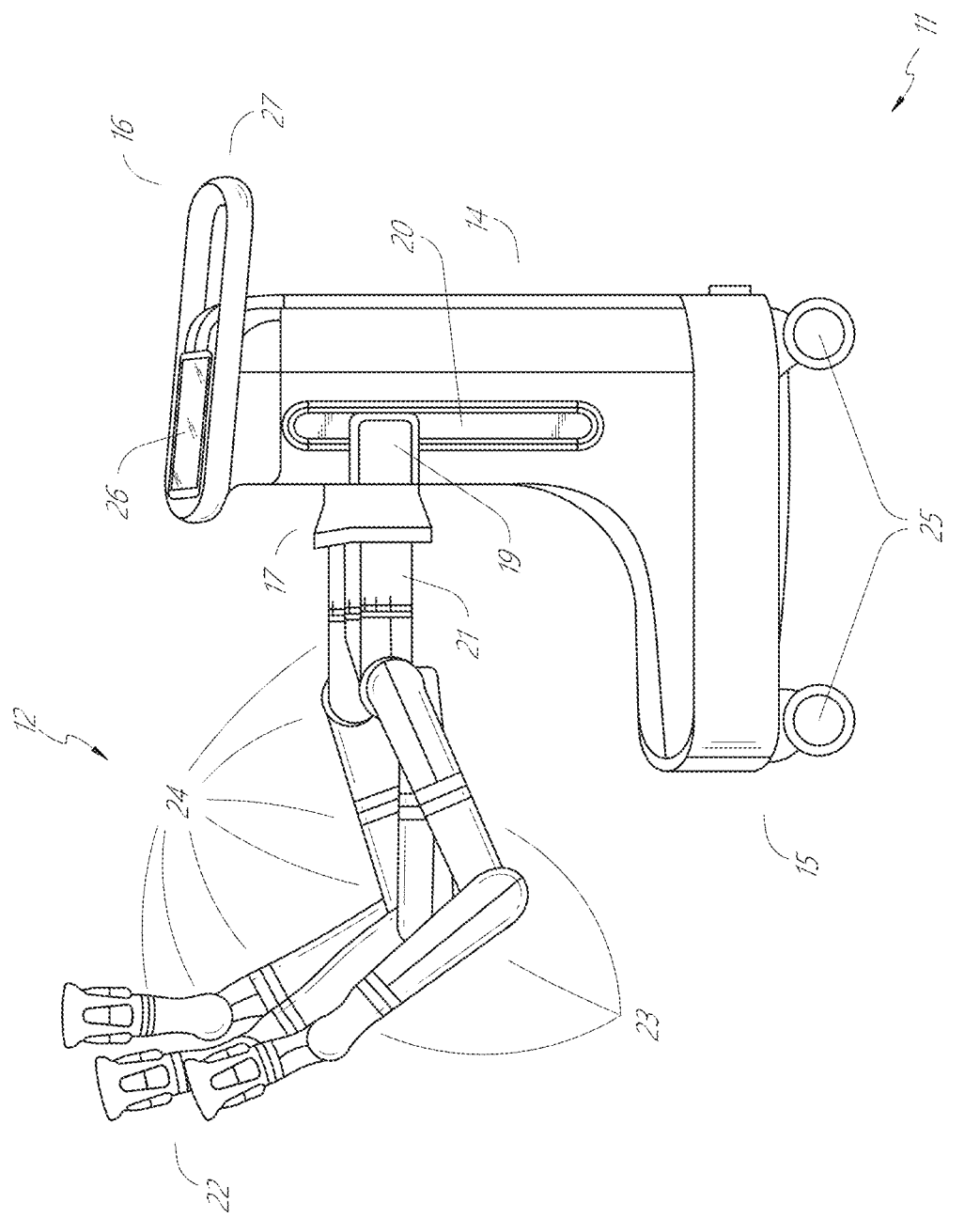
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
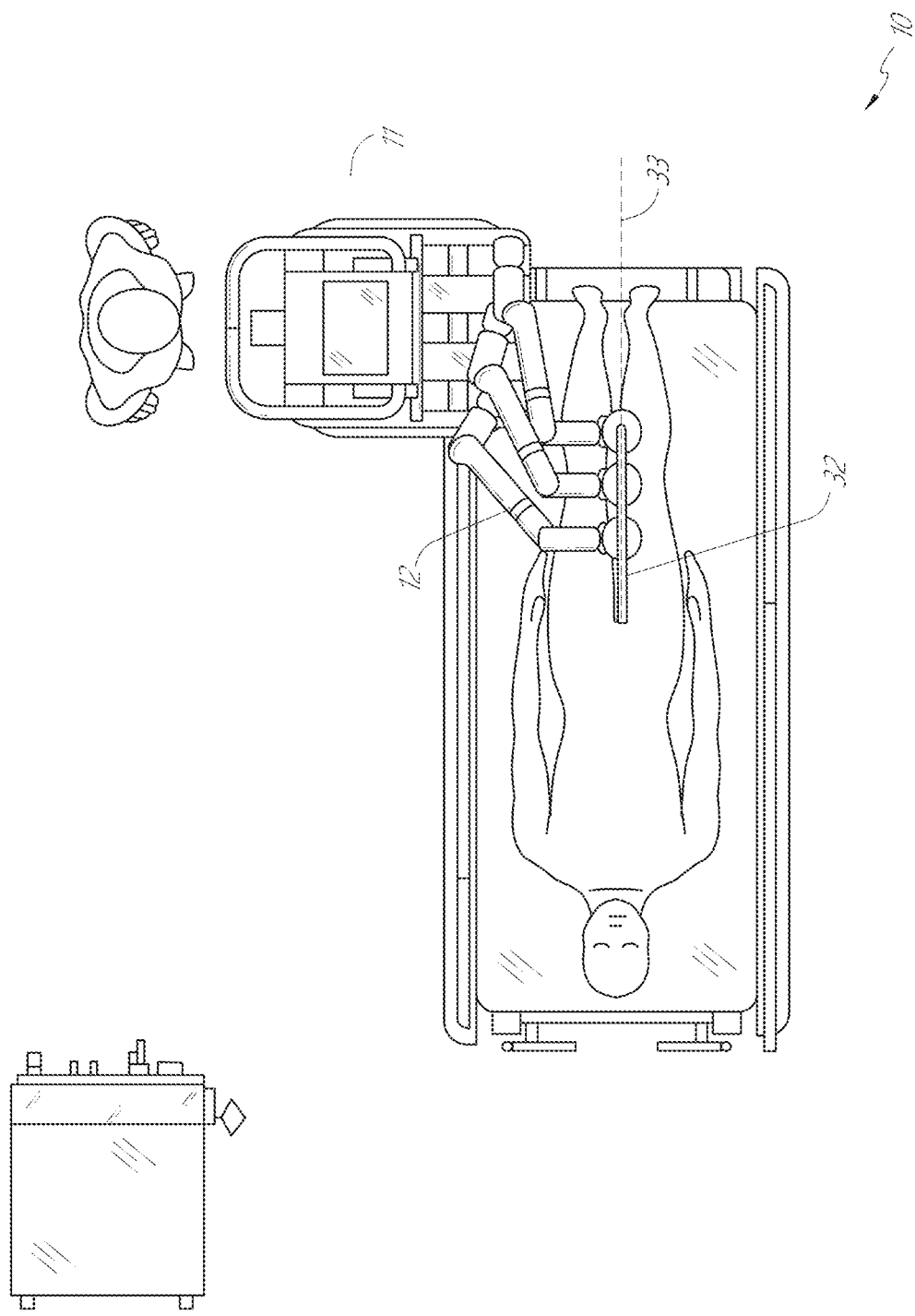
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
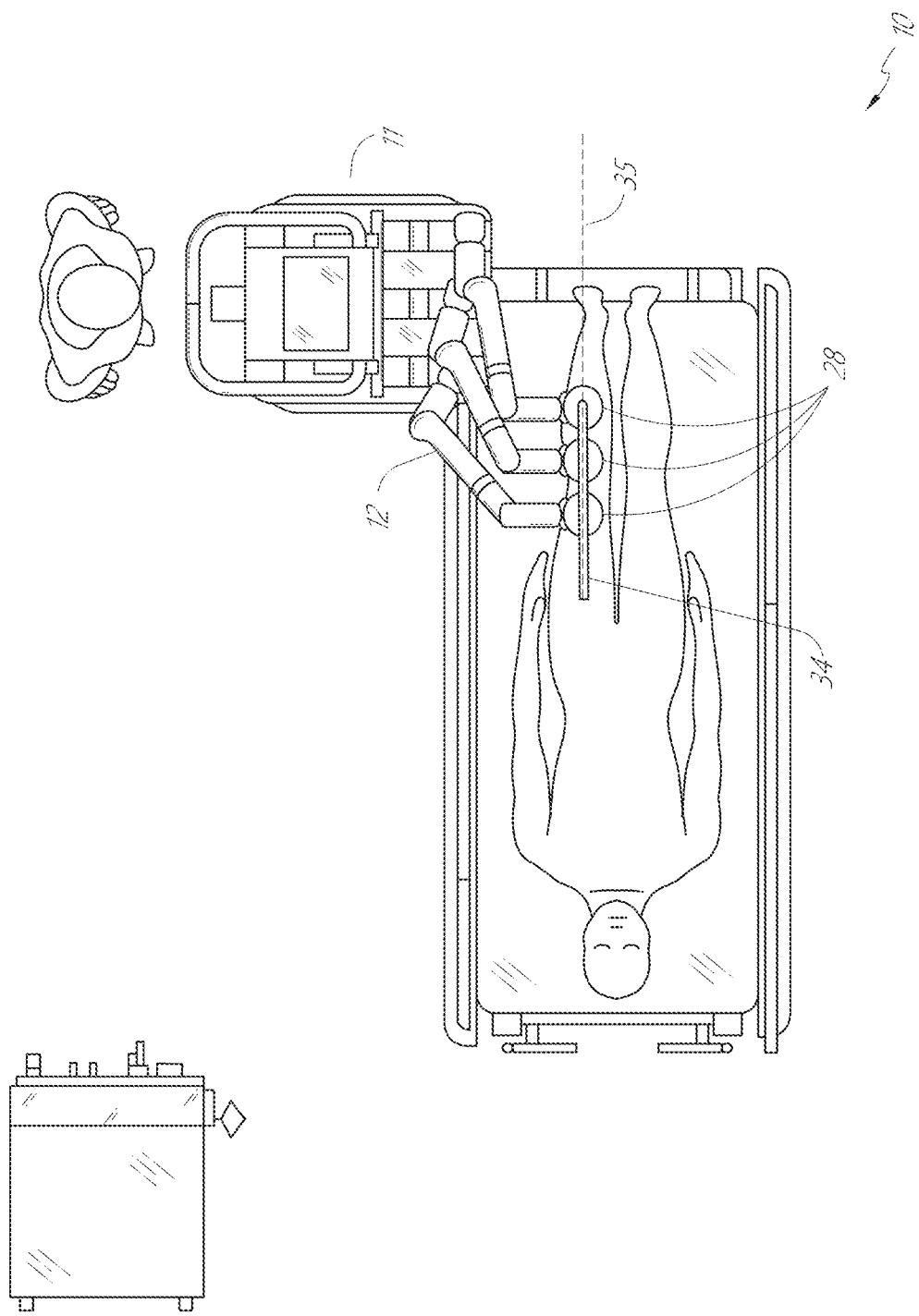
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
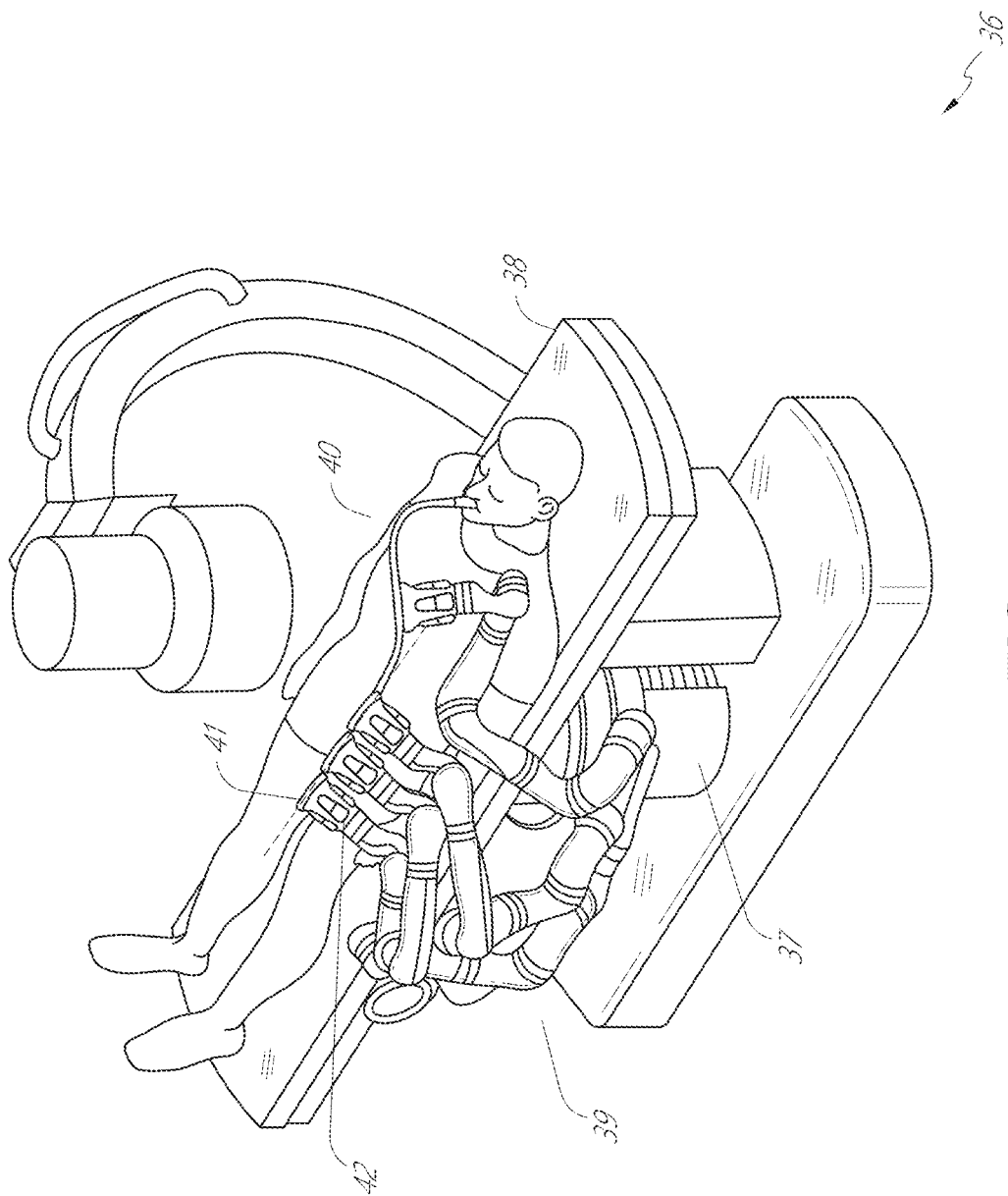
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
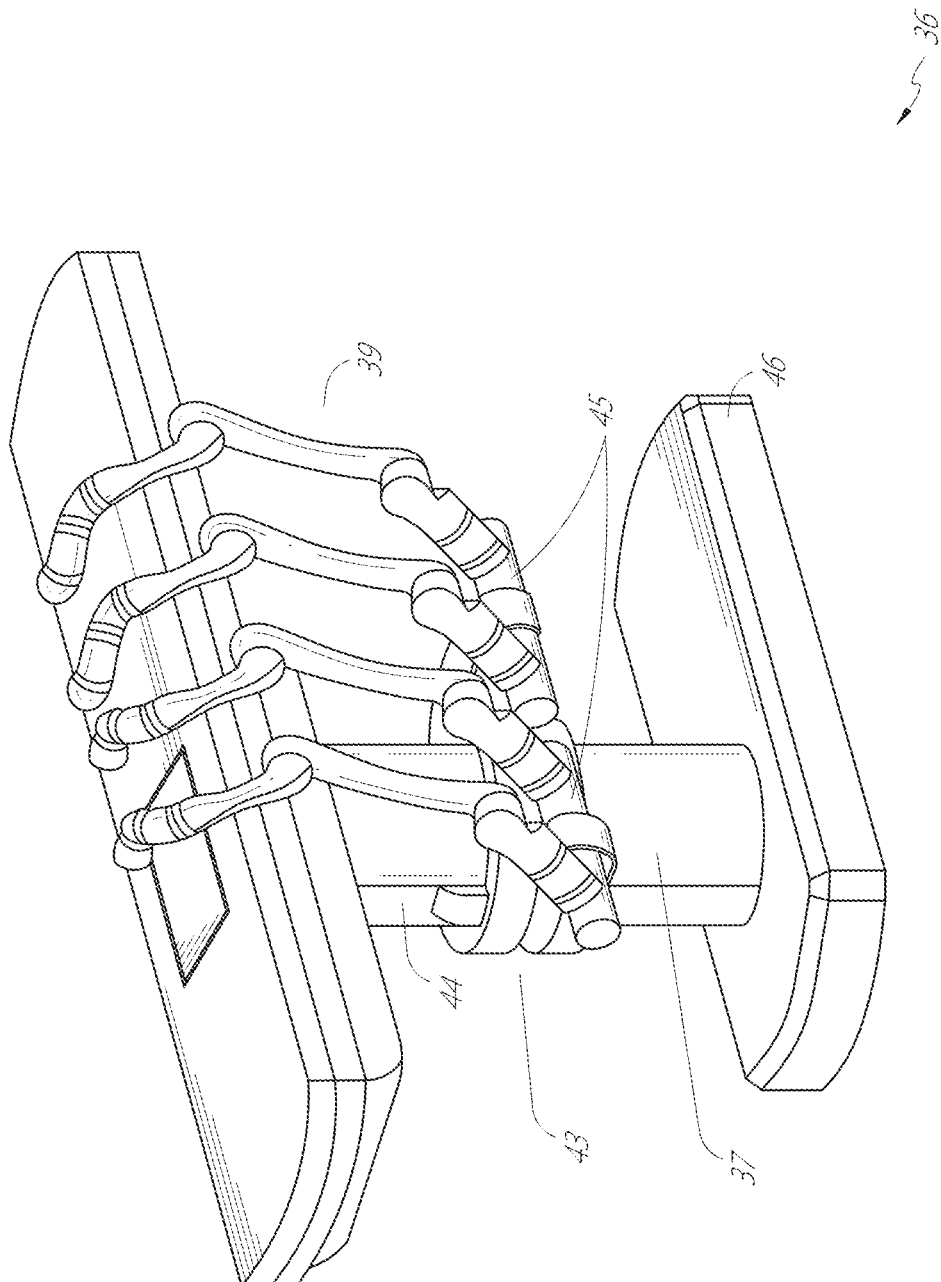
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
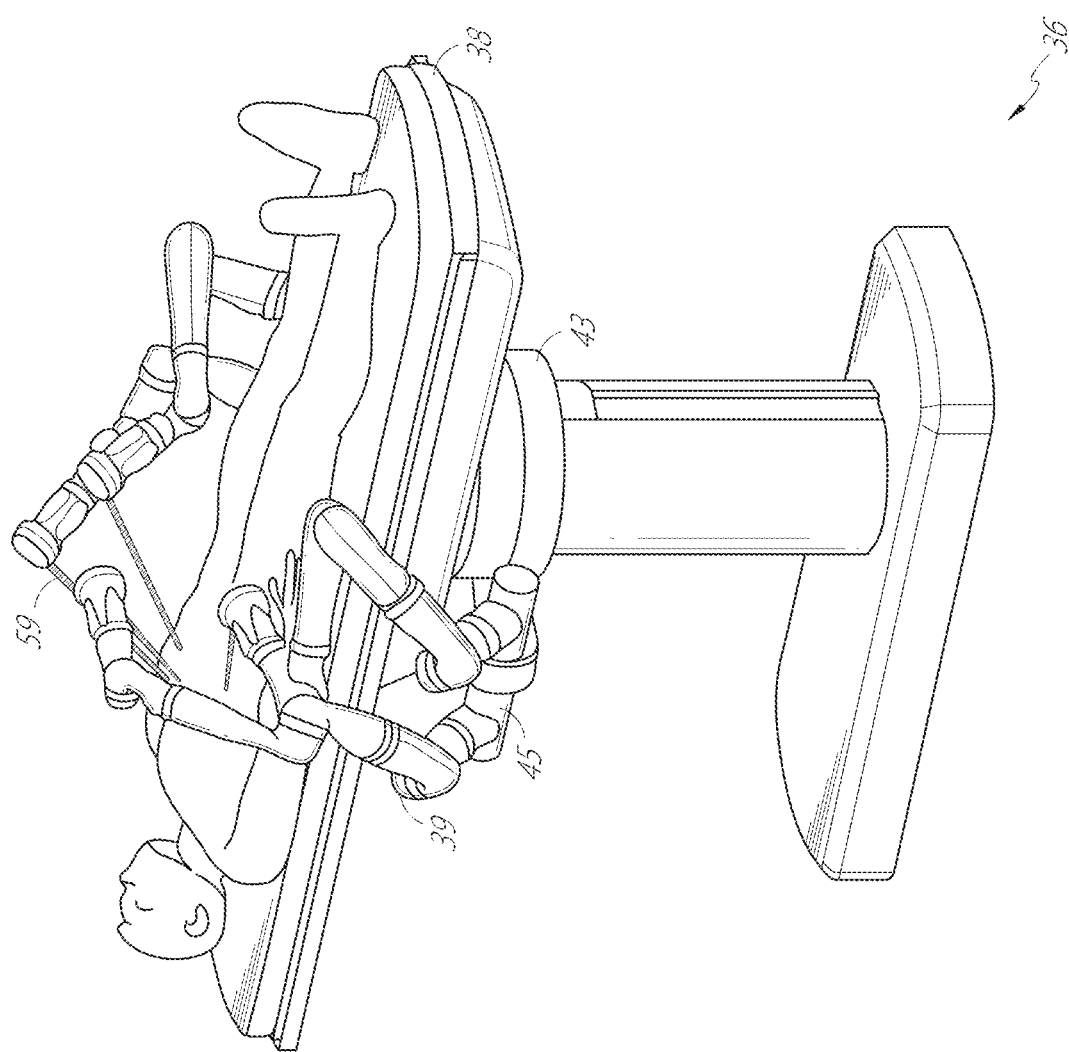
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
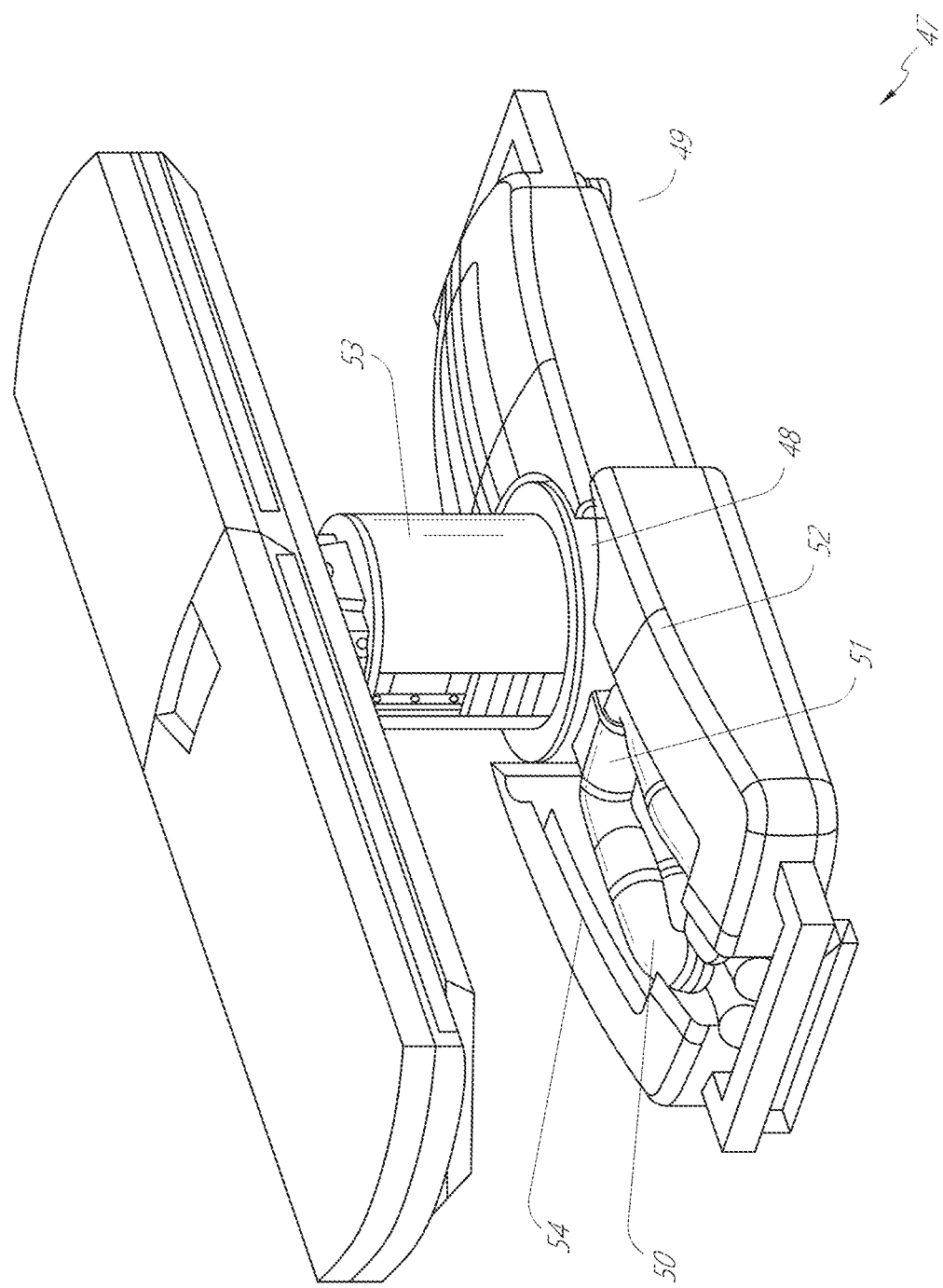
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
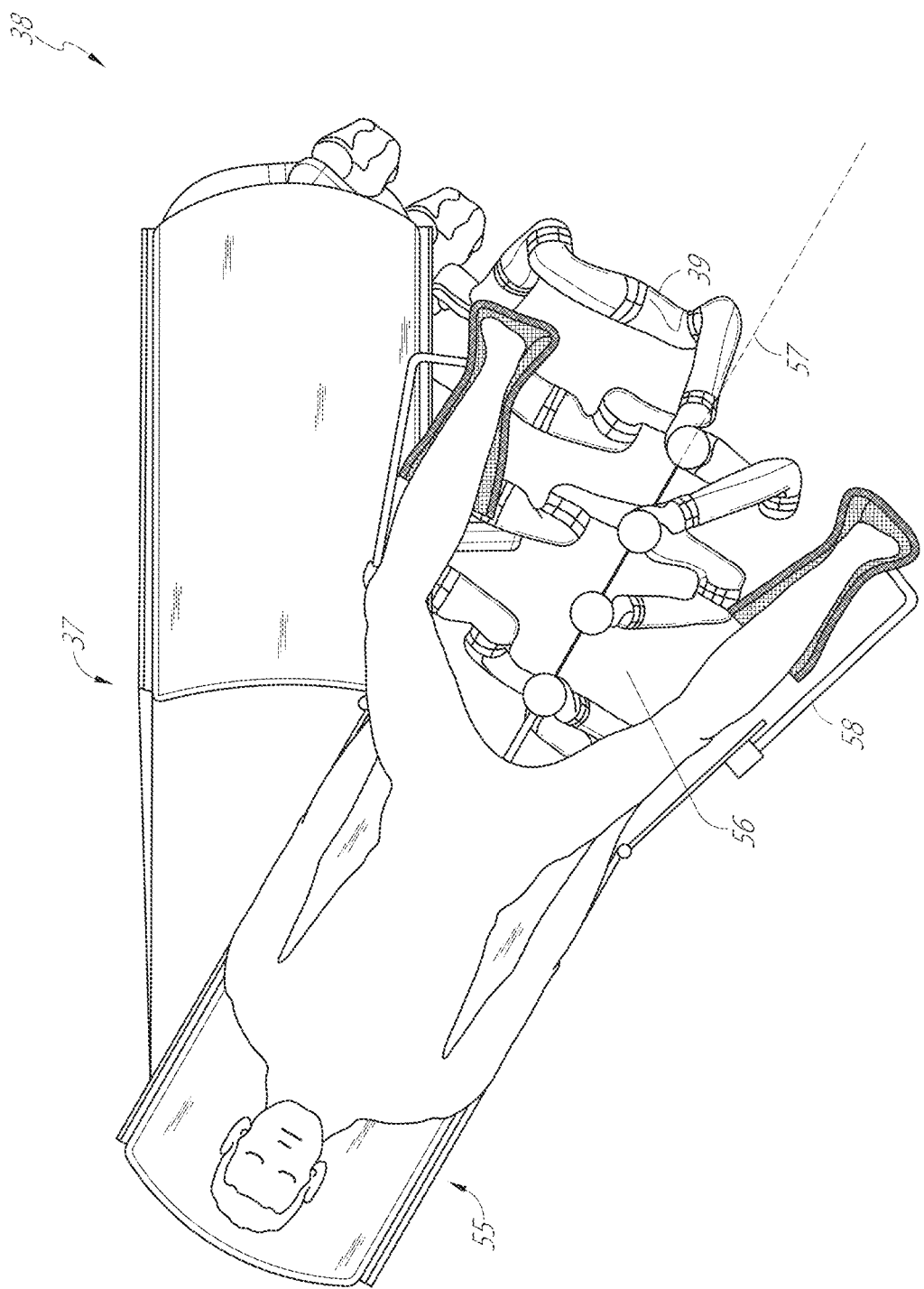
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments, often referred to as laparoscopes, may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instruments 59 may be positioned using the arm mounts 45 to be passed through minimal incisions on both sides of the patient to reach his/her abdominal cavity.

Figure 10:
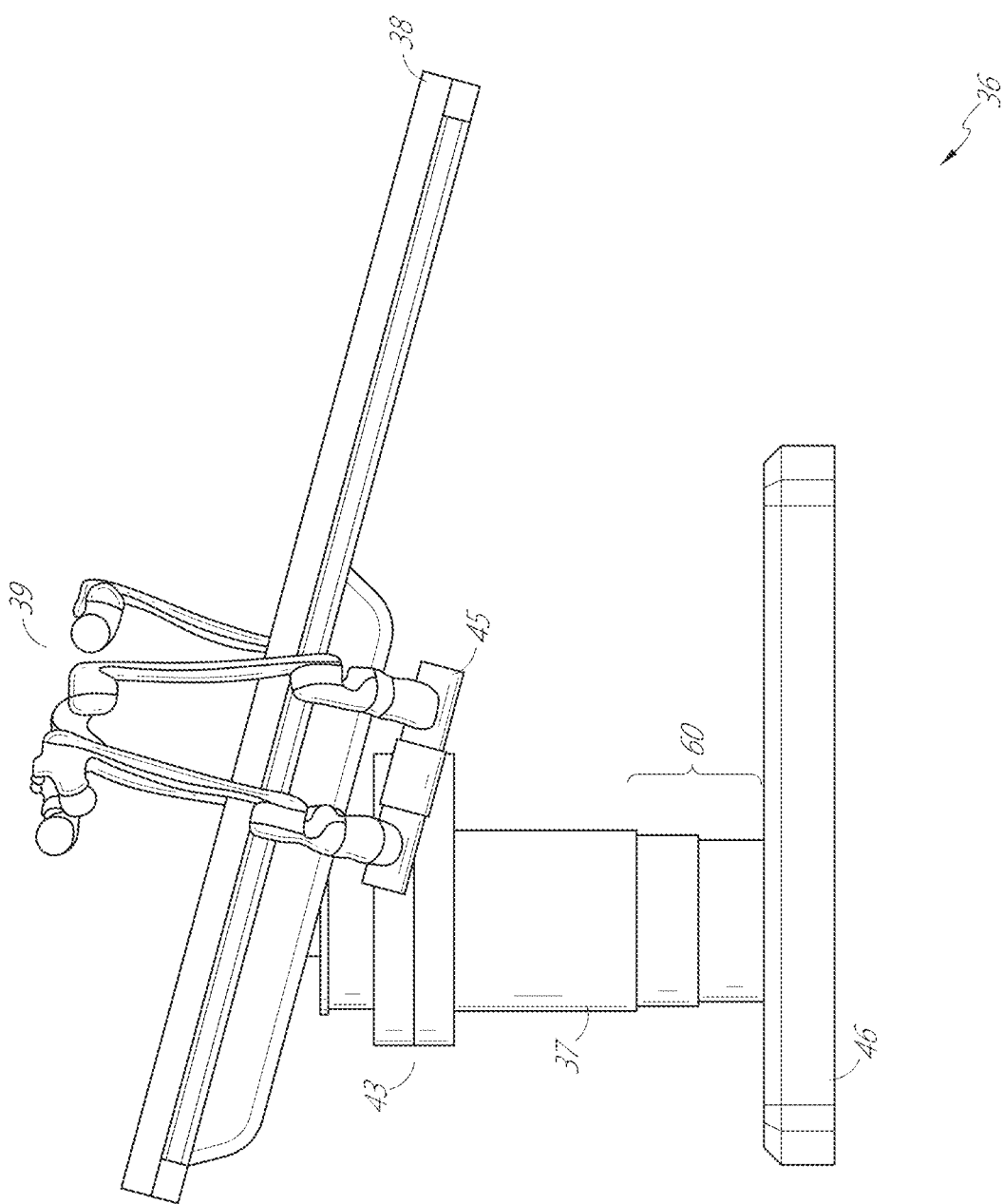
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
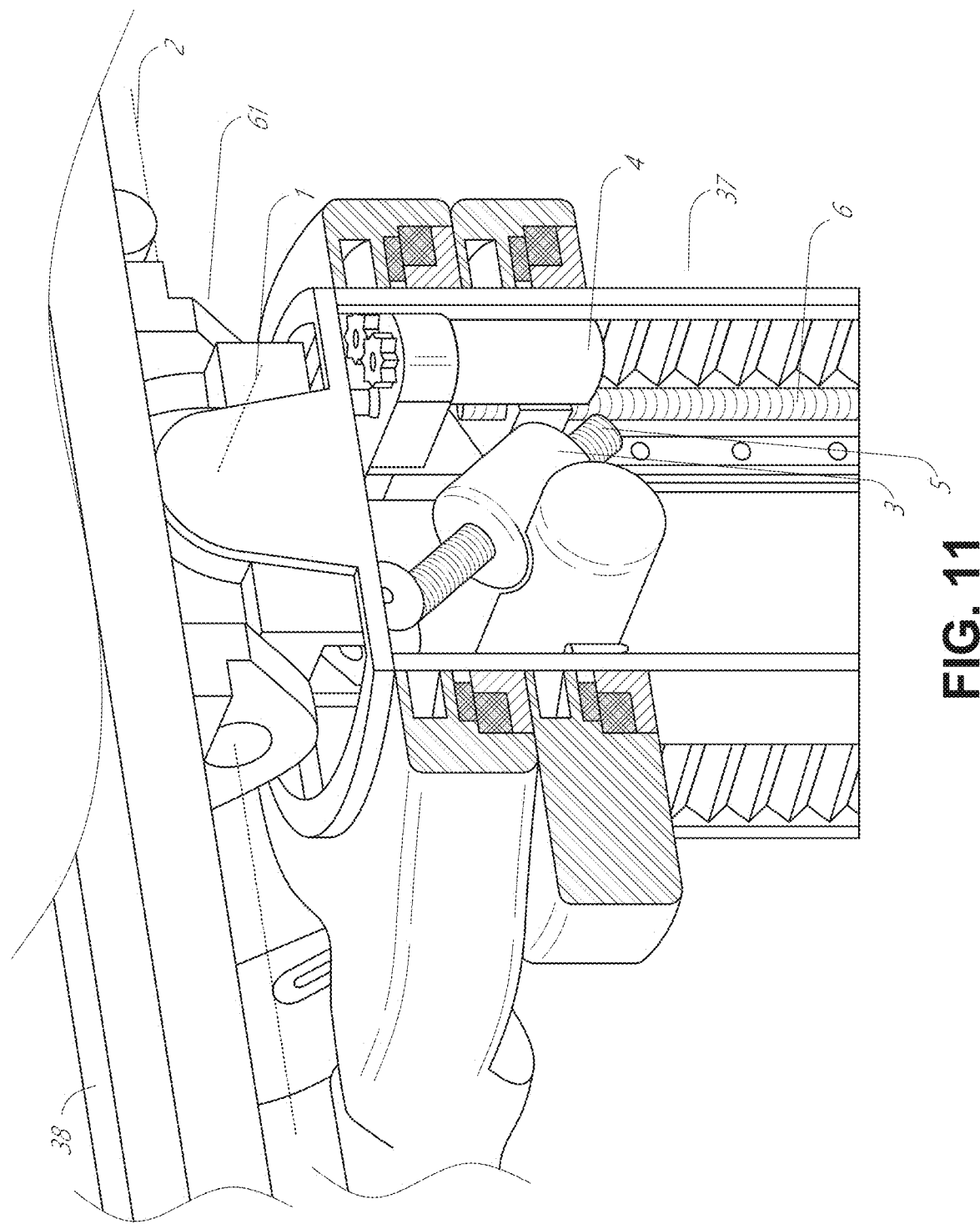
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
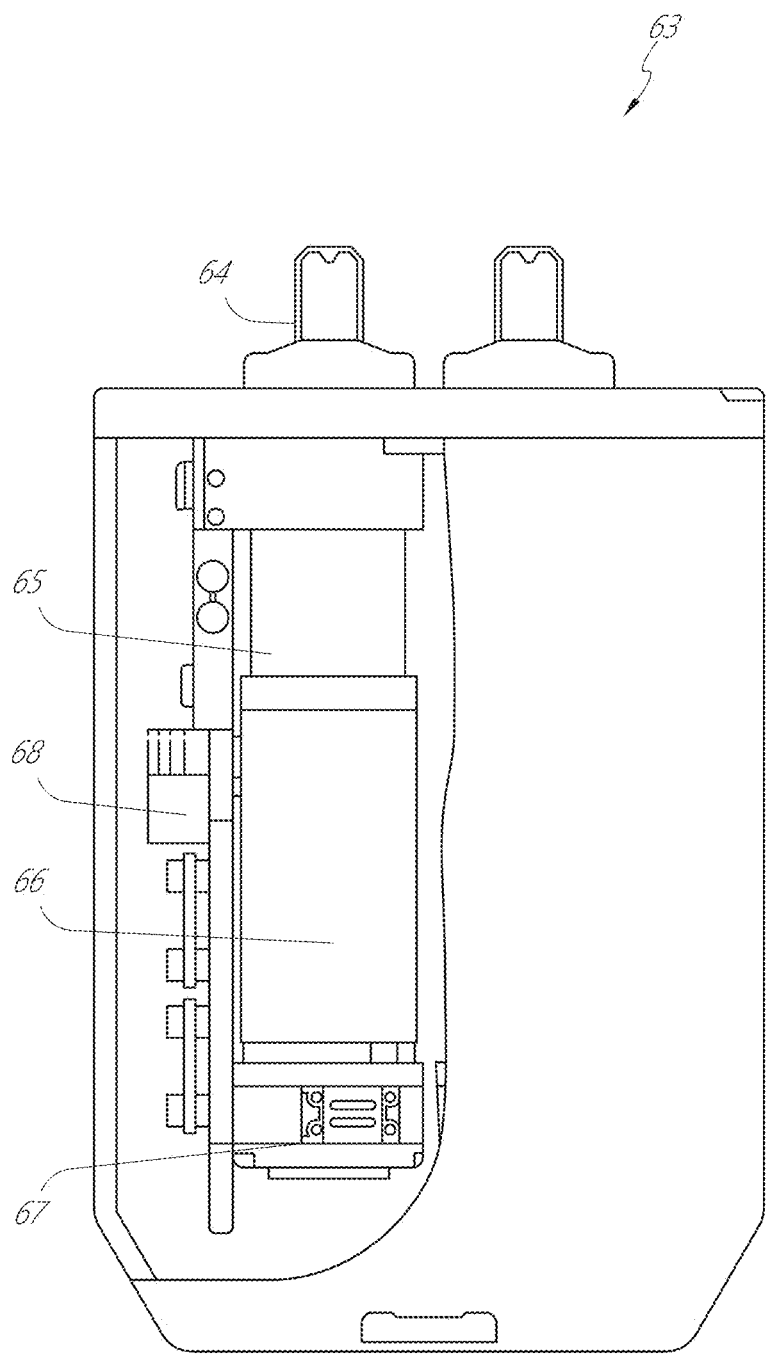
FIG. 12 illustrates an exemplary instrument driver.

FIG. 12 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 13:
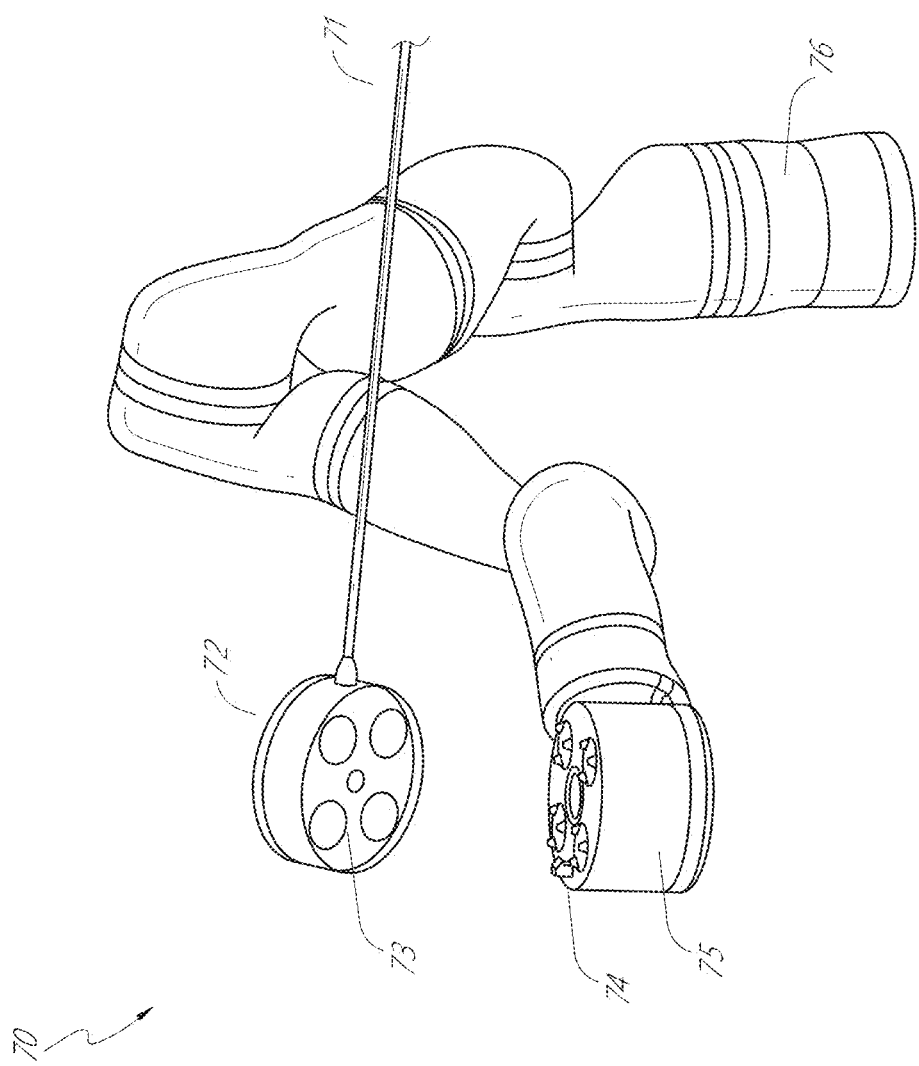
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 66 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at a distal portion of the elongated shaft. During a procedure, such as a laparoscopic, endoscopic, or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongate shaft during an endoscopic procedure.

Figure 14:
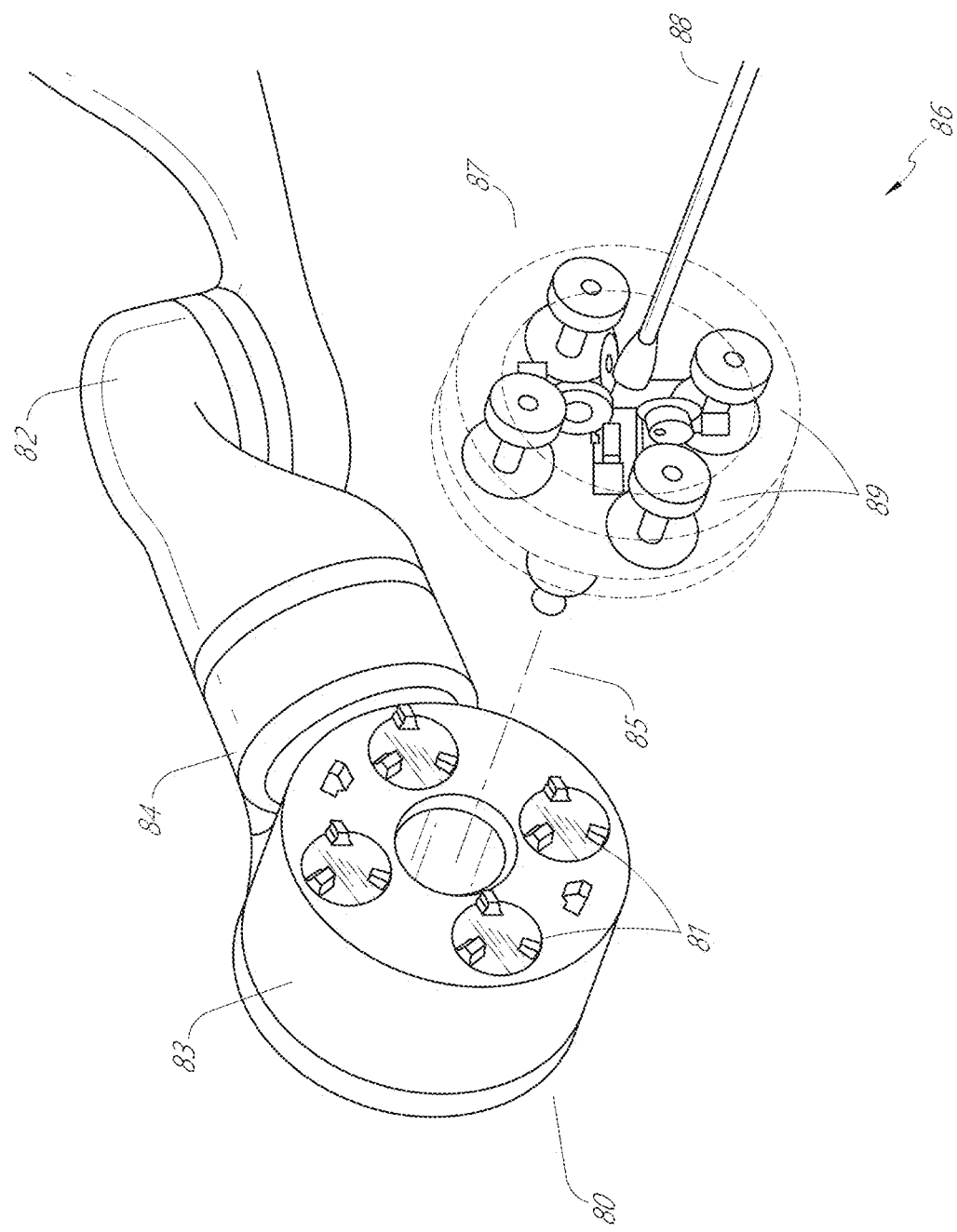
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
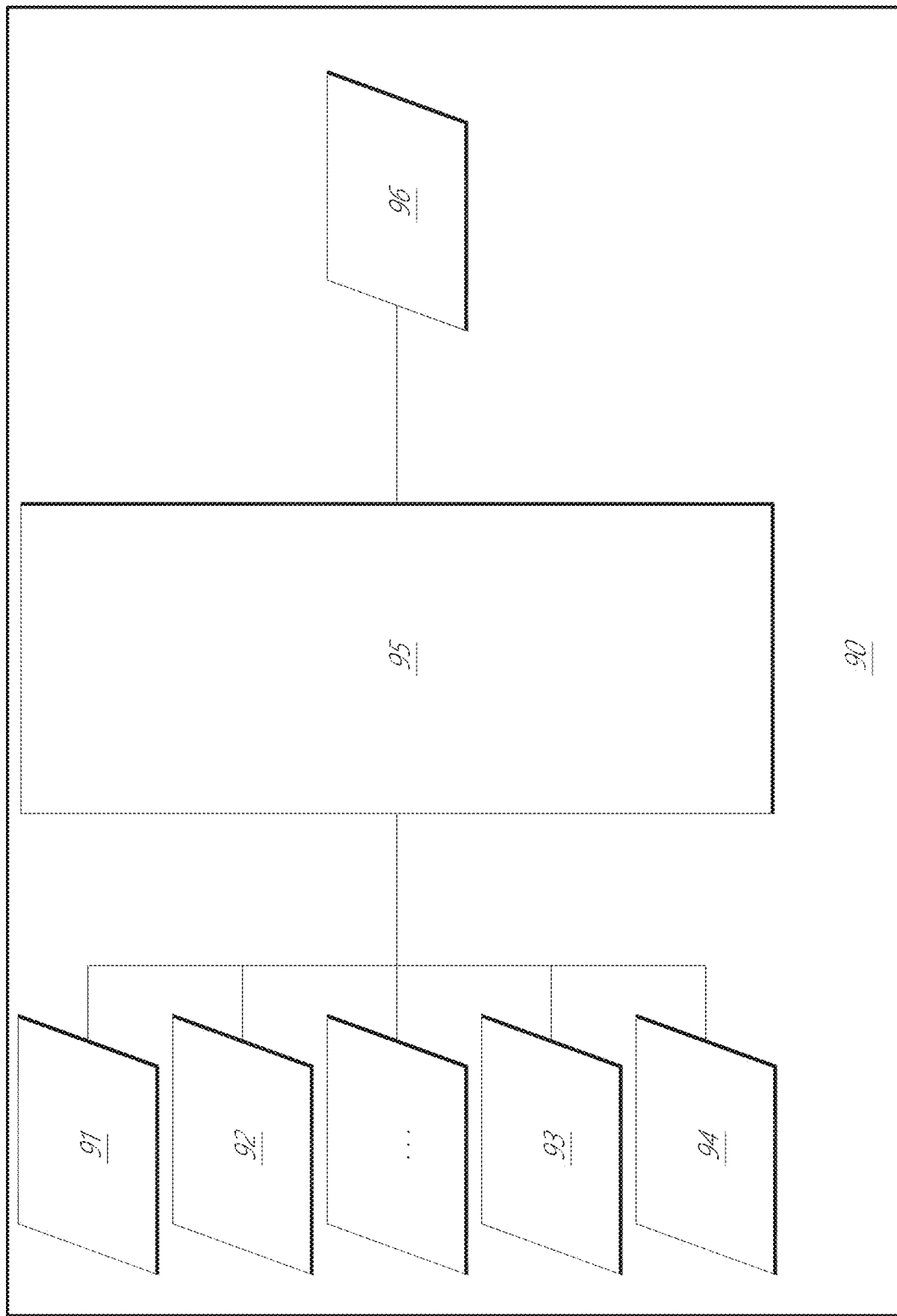
FIG. 15 depicts a block diagram illustrating a localization system that estimates a location of one or more elements of the robotic systems of FIGS. 1-10, such as the location of the instrument of FIGS. 13-14, in accordance to an example embodiment.

FIG. 15 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g., as "slices" of a cutaway view of the patient's internal anatomy. When analyzed in the aggregate, image-based models for anatomical cavities, spaces and structures of the patient's anatomy, such as a patient lung network, may be generated. Techniques such as centerline geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Navigation Path Tracing

Embodiments of the disclosure relate to systems and techniques for navigation path tracing. Navigation path tracing can be used to generate and display visual indicia indicative of a historical path (e.g., breadcrumbs) of a medical instrument as the instrument is navigated through a luminal network. As the instrument is navigated through the luminal network, the position of the instrument can be determined and visual indicia indicative of the position of the instrument can be displayed (e.g., plotted or otherwise displayed). The visual indicia can aid a user in visualizing which portions of the luminal network have already been explored or navigated by the instrument. The visual indicia can also be used to visualize the shape of the luminal network and/or extend a preoperative model of the luminal network.

A. Example Luminal Networks and Preoperative Models.

Figure 16:
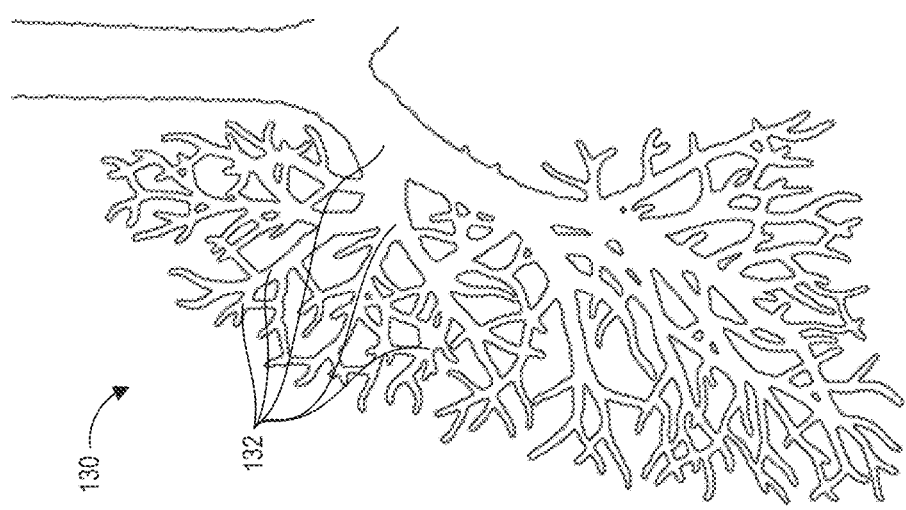
FIG. 16 illustrates an example luminal network that can be navigated by a robotically controlled medical instrument.

FIG. 16 illustrates an example luminal network 130 of a patient that can be navigated using the navigation path tracing methods and systems described herein. In the illustrated embodiment, the luminal network 130 is a bronchial network of airways inside a patient's lung. As illustrated, the luminal network 130 comprises a plurality of lumens 132 that are arranged in a branched structure. Although the illustrated luminal network 130 comprises a plurality of branched lumens 132, in some instances, the luminal network 13 may comprise only a single lumen 132. That is, in some instances, a luminal network 130 need not comprise a branched arrangement of lumens 132. For ease of illustration, FIG. 16 represents the luminal network 130 as a two-dimensional structure. This should not be construed to limit the present disclosure to two-dimensional luminal networks in any way. In general, the luminal network 130 comprises a three-dimensional structure.

Figure 17:
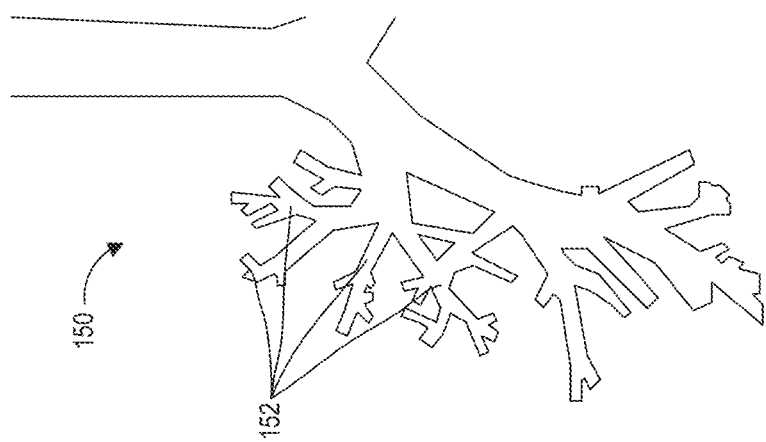
FIG. 17 illustrates an example preoperative model of the luminal network of FIG. 16.

Although a particular luminal network 130 is illustrated in FIG. 17, the navigation path tracing methods and systems described herein can be implemented during navigation of a wide variety of luminal networks 130. Such luminal network 130 can include, for example, bronchial networks, renal networks, cardiovascular networks (e.g., arteries and veins), gastrointestinal tracts, urinary tracts, etc. The navigation path tracing methods and systems described herein can be implemented during navigation of both branched and non-branched luminal networks 130.

FIG. 17 illustrates an example preoperative model 150 of the luminal network 130 of FIG. 16. As will be described in greater detail below, in some instances, the preoperative model may be used to facilitate navigation of a medical instrument through the luminal network 130. In some instances, the preoperative model 150 may be displayed to a user prior to and/or during navigation of the luminal network 130.

The preoperative model 150 may be representative of one or more portions of the luminal network 130 that is being navigated by the medical instrument. In some implementations, the preoperative model 150 may be generated prior to navigation of the luminal network using one or more of various preoperative imaging and mapping techniques. As one example, preoperative mapping may be accomplished through the use of a collection of low dose CT scans. As discussed above, preoperative CT scans can generate two-dimensional images, each representing a "slice" of a cut-away view of the patient's internal anatomy. When analyzed in the aggregate, image-based preoperative models for anatomical cavities, spaces, and structures of the patient's anatomy, such as a patient lung network (i.e., a luminal network), may be generated. Other methods for generating the preoperative model 150 are also possible.

In the illustrated embodiment, the preoperative model 150 comprises a plurality of segments 152. The segments 152 of the preoperative model 150 correspond with at least a portion of the lumens 132 of the luminal network 130. Thus, if the luminal network 130 comprises a branched arrangement of lumens 132, the preoperative model 150 can comprise a corresponding branched arrangement of segments 152. If the luminal network 130 comprises a single lumen 132, the preoperative model 150 can comprise a corresponding single branch 152. In general, the preoperative model 150 comprises a three-dimensional shape, corresponding to at least a portion of the three-dimensional shape of the luminal network 130. Although the preoperative model 150 may comprise a three-dimensional shape, FIG. 17 illustrates the preoperative model 150 as a two-dimensional shape for ease of illustration. In some instances, a cross-section of a three-dimensional preoperative model 150 may be displayed on a two-dimensional display.

Comparing the luminal network 130 of FIG. 16 and the preoperative model 150 of FIG. 17, it can be seen that, in some instances, the preoperative model 150 may represent or correspond to only a portion of the luminal network 130. This is further illustrated in FIG. 18, which is a view of the preoperative model 150 overlaid on the luminal network 130. In some instances, limitations in the preoperative imaging and mapping techniques used to generate the preoperative model 150 may prevent generation of a model that corresponds to the entire luminal network 130. For example, certain branched lumens 132 within the luminal network may be sufficiently small that they cannot be clearly depicted and analyzed with common preoperative imaging and mapping techniques. As such, the preoperative model 150 may not provide a complete representation of the luminal network 130, for example, leaving various portions of the luminal network 130 unmapped and/or unrepresented in the preoperative model 150.

Figure 18:
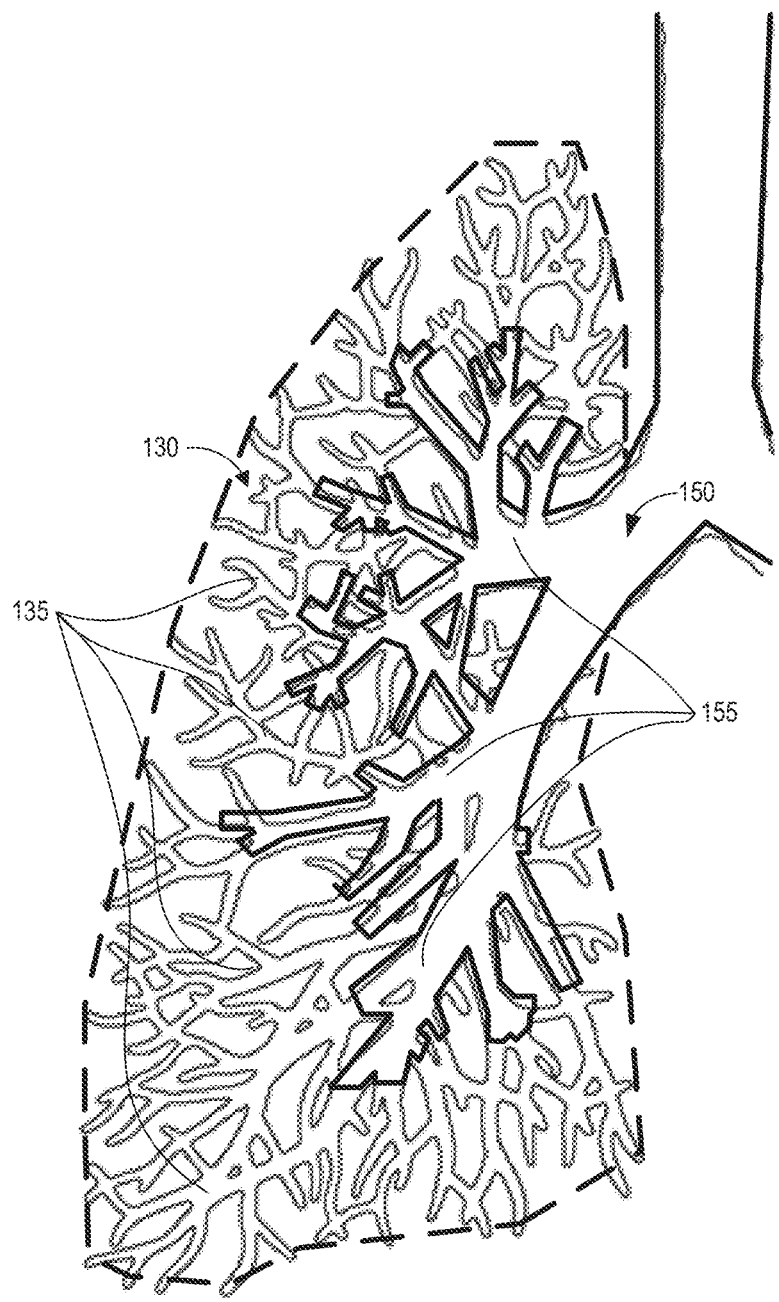
FIG. 18 is a view of the preoperative model of FIG. 17 overlaid on the luminal network of FIG. 16 and illustrates that the preoperative model corresponds to a mapped portion of the luminal network.

For example, as shown in FIG. 18, the preoperative model 150 can correspond to a mapped portion 155 of the luminal network 130. An unmapped portion 135 of the luminal network 130, which may not represented by the preoperative model 150, may extend beyond the mapped portion 155.

In some embodiments, the preoperative model 150 may also include a representation of an outer surface of the organ that includes the luminal network. For example, in the case of the a lung, a preoperative model may include a representation of at least a portion of the airways and also an exterior surface of the lung.

B. Navigation of a Luminal Network with a Medical Instrument.

Figure 19:
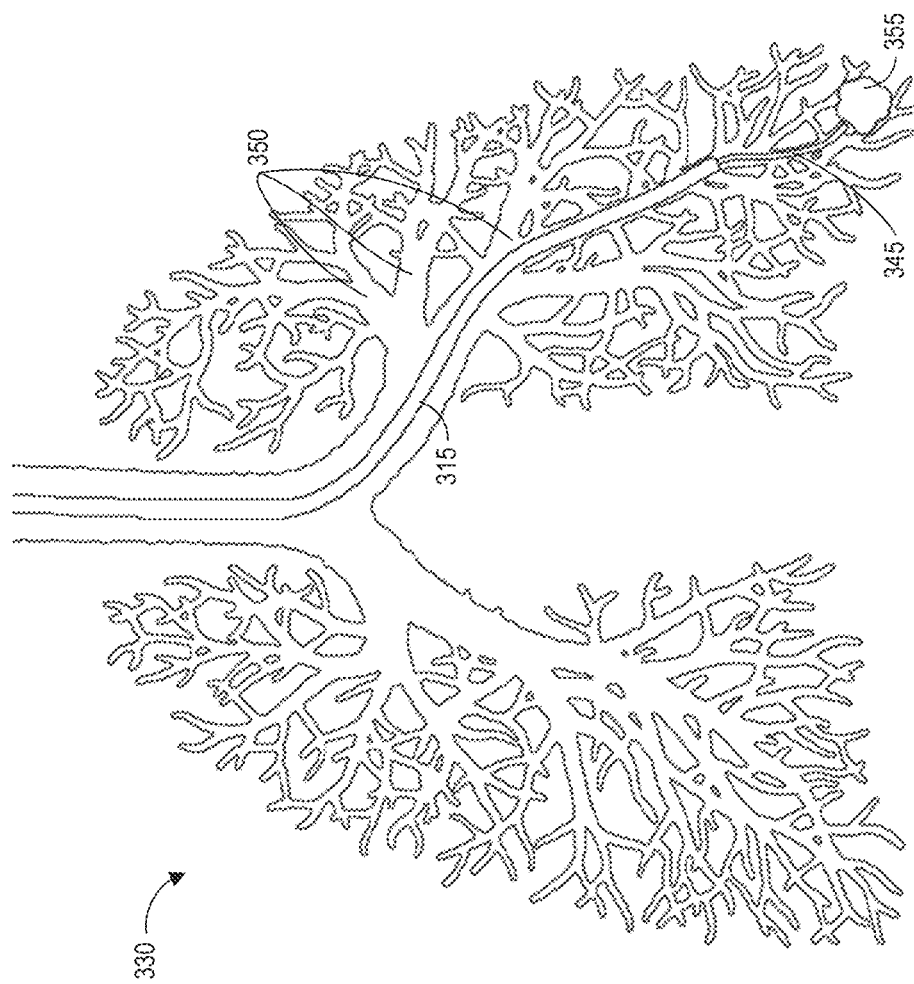
FIG. 19 provides an example of a medical instrument navigating within a luminal network.

FIG. 19 provides an example of a medical instrument (e.g., endoscope 315 and catheter 345) navigating within a luminal network 330. As illustrated, the luminal network 330 (which may be similar to the luminal network 130 described above) includes a branched structure of airways 350 (which may be similar to lumens 132). In this example, the endoscope 315 is navigated (e.g., directed, guided, moved, etc.) through the luminal network 330 towards an area of interest (e.g., nodule 355) for diagnosis and/or treatment. In the illustrated example, the nodule 355 is located at a periphery of the luminal network 330 and airways 350. The endoscope 315 has a first diameter and thus its distal end may not be able to be positioned through the smaller-diameter airways around the nodule 355. Accordingly, a steerable catheter 345 can extend from a working channel of the endoscope 315 the remaining distance to the nodule 355. The steerable catheter 345 may have a lumen through which instruments, such as biopsy needles, cytology brushes, tissue sampling forceps, etc., can be passed to the target tissue site of nodule 355. In such implementations, both the distal end of the endoscope 315 and the distal end of the steerable catheter 345 can be provided with EM instrument sensors (or other position sensors) for tracking their position within the airways 350. In other embodiments, the overall diameter of the endoscope 315 may be small enough to reach the periphery without the steerable catheter 345, or may be small enough to get close to the periphery (e.g., within 2.5-3 cm) to deploy medical instruments through a non-steerable catheter. The medical instruments deployed through the endoscope 315 may be equipped with EM instrument sensors (or other position sensors).

As mentioned above, in the example of FIG. 19, the nodule 355 is positioned at the periphery of the luminal network 330. This may be in an area of the luminal network 330 that is not represented by the preoperative model 150. That is, the nodule 355 may, in some instances, be positioned within the unmapped portion 135 of the luminal network 130, 330.

Figure 20:
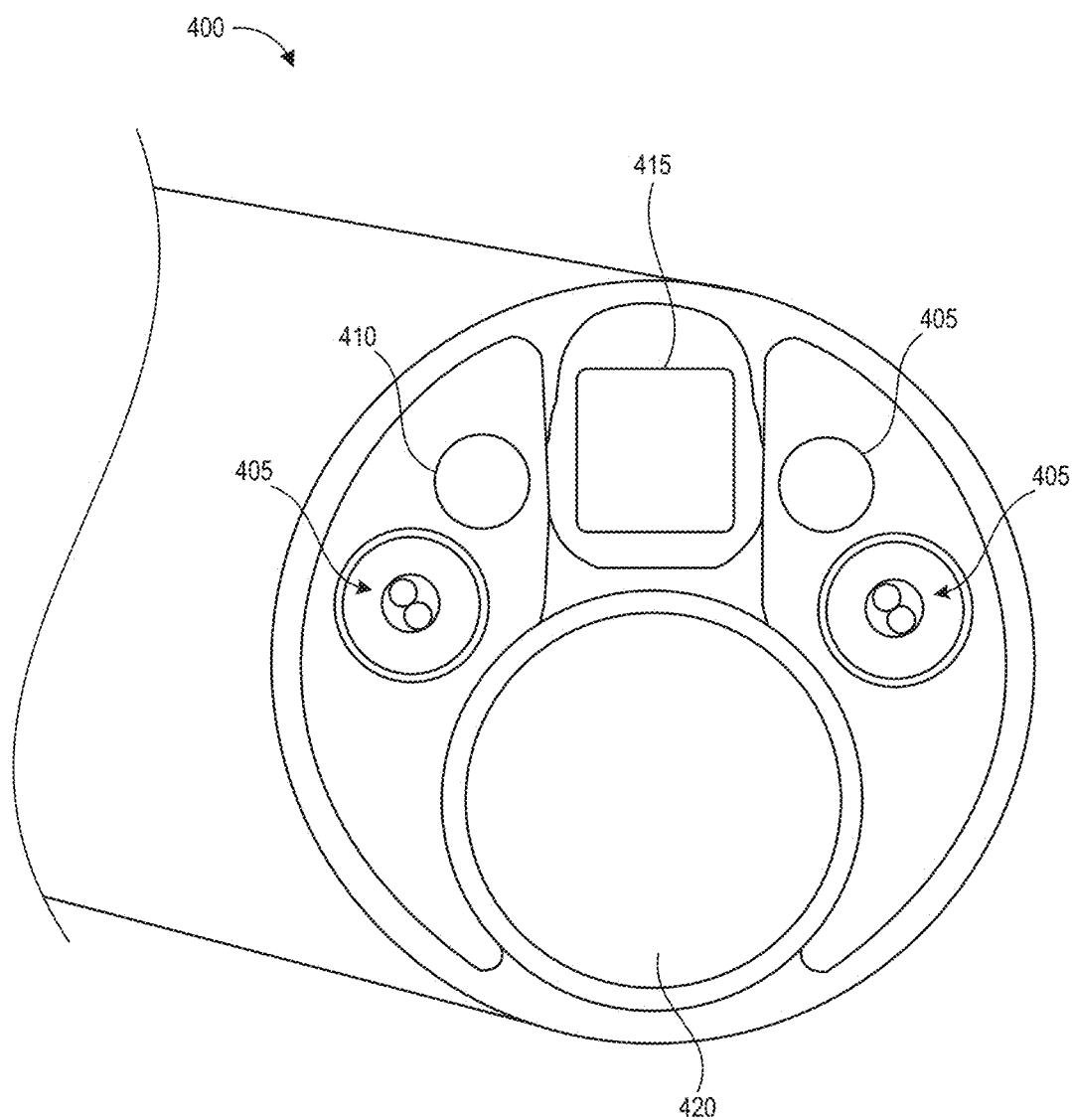
FIG. 20 illustrates a detail view of a distal end of an example medical instrument.

FIG. 20 illustrates a detail view of a distal end of an example medical instrument 400. The medical instrument 400 be representative of the endoscope 315 or steerable catheter 345 of FIG. 19. The medical instrument 400 may be representative of any medical instrument described throughout the disclosure, such as the endoscope 13 of FIG. 1, the ureteroscope 32 of FIG. 3, the laparoscope 59 of FIG. 9, etc. In FIG. 19, the distal end of the instrument 400 includes an imaging device 415, illumination sources 410, and ends of EM sensor coils 405, which form an EM instrument sensor. The distal end further includes an opening to a working channel 420 of the instrument through which surgical (or medical) instruments, such as biopsy needles, cytology brushes, forceps, etc., may be inserted along the instrument shaft, allowing access to the area near the instrument tip.

EM coils 405 (also referred to as EM position sensors 405) located on the distal end of the instrument 400 may be used with an EM tracking system (see FIG. 21 described below) to detect the position and orientation of the distal end of the instrument 400 while it is positioned within a luminal network. In some embodiments, the coils 405 may be angled to provide sensitivity to EM fields along different axes, giving the disclosed navigational systems the ability to measure a full 6 degrees of freedom (DoF): three positional DoF and three angular DoF. In other embodiments, only a single coil 405 may be disposed on or within the distal end with its axis oriented along the instrument shaft. Due to the rotational symmetry of such a system, it may be insensitive to roll about its axis, so only five degrees of freedom may be detected in such an implementation. The EM coils may be configured to provide EM data 93 (see FIG. 15) from which the navigation and localization system 90 can determine or estimate the position of the instrument. In some embodiments, the EM coils 405 can be replaced with or used in addition to other types of positions sensors for detecting the position of the instrument 400.

Figure 21:
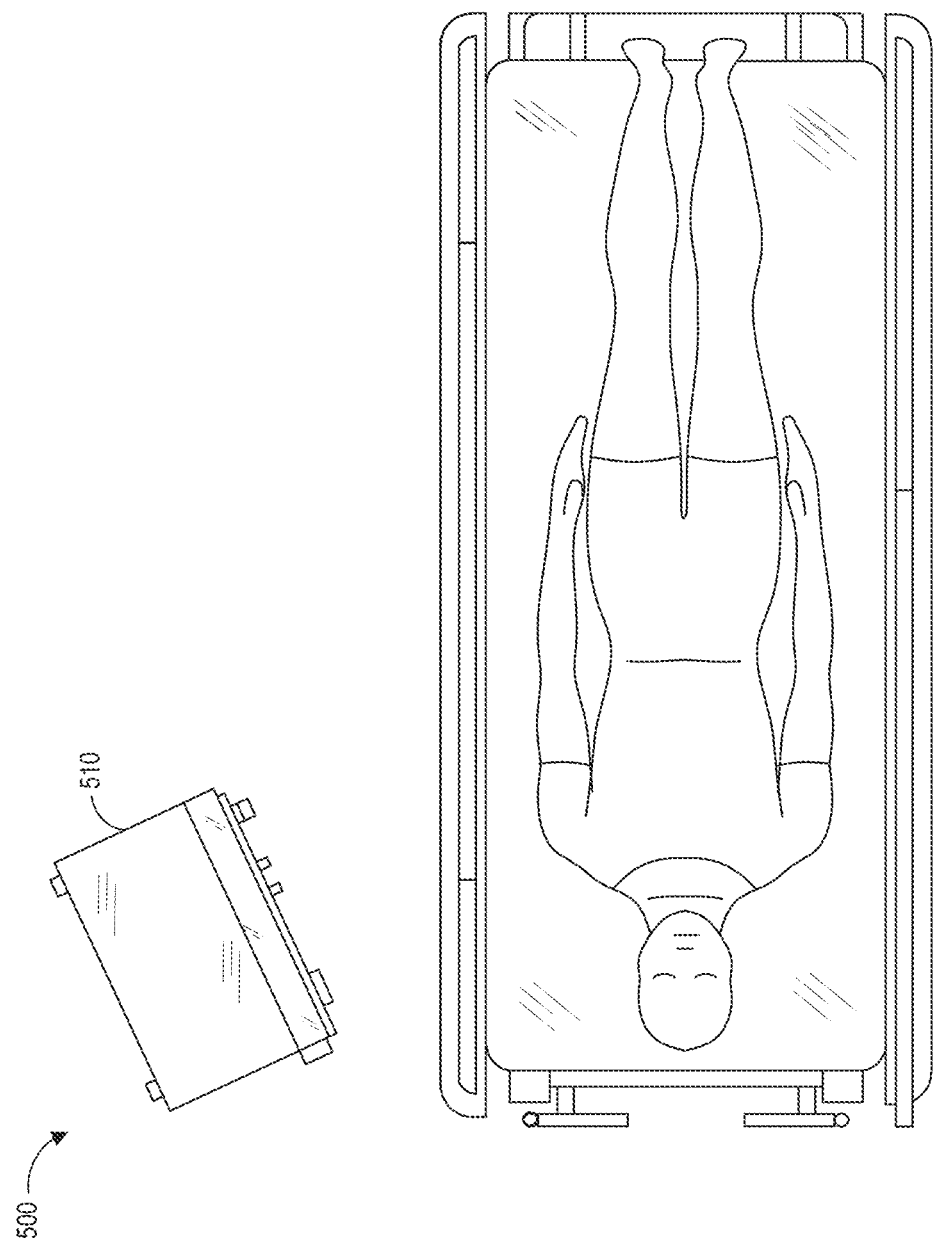
FIG. 21 illustrates certain components of an example electromagnetic (EM) system for determining position of a medical instrument.

FIG. 21 illustrates certain components of an example electromagnetic (EM) system 500 for determining position of a medical instrument based on EM data 93 generated by EM coils 405. The system 500 can include an EM field generator 510 and EM coils 405 positioned on the instrument 400. The system 500 can be implemented in an operating environment that includes a table for supporting a patient. Certain additional devices/elements may also be included, but have not been illustrated in FIG. 21. For example, the environment may also include: a robotic system configured to guide movement of the medical instrument, a command center/console for controlling operations of the surgical (or medical) robotic system, and an EM controller. The EM controller may further be connected to the EM field generator 510 to provide control signals thereto for generating an EM field. In certain embodiments, the EM controller may be partially or completely incorporated into one or more of the other processing devices of the system, including the EM field generator 510, the cart 11 (see FIG. 1), the tower 30 (see FIG. 1), etc.

When included, the EM controller may control EM field generator 510 to produce a an EM field. The EM field may be a varying EM field. The EM field may be time-varying and/or spatially varying, depending upon the embodiment. The EM field generator 510 may be located on a cart, similar to the cart 11 illustrated in FIG. 2, or may be attached to a rail of the table via one or more supporting columns. In other embodiments, an EM field generator 510 may be mounted on a robotic arm, for example similar to those shown in surgical (or medical) robotic system 10 of FIG. 1, which can offer flexible setup options around the patient.

An EM spatial measurement system may determine the location of objects within the EM field that are embedded or provided with EM sensor coils, for example, the EM coils 405 (as shown in FIG. 20). When an EM sensor is placed inside a controlled, varying EM field as described herein, voltages are induced in sensor coil(s) included in the EM sensor. These induced voltages can be used by the EM spatial measurement system to calculate the position and orientation of the EM sensor and thus the object having the EM sensor. As the EM fields are of a low field strength and can safely pass through human tissue, location measurement of an object is possible without the line-of-sight constraints of an optical spatial measurement system.

The EM field may be defined relative to a coordinate frame of the EM field generator 510, and a coordinate frame of the preoperative model 150 of the luminal network 130 can be mapped (or registered) to the coordinate frame of the EM field. Thus, the position of the instrument, as determined by the position of the EM instrument sensors 405 on the instrument within the EM field can be determined within the coordinate frame of the preoperative model, but without relying on the preoperative model to determine the position.

The system 500 may thus return EM data 93 that can be used by the localization system 90 to determine the position of the instrument. As noted above, this EM data 93 can provide a modality that can be used to determine position in a coordinate frame that has been mapped or registered to the preoperative model 150.

Returning to FIG. 20, the instrument 400 may also include illumination sources 410. The illumination sources 410 provide light to illuminate a portion of an anatomical space. The illumination sources can each be one or more light-emitting devices configured to emit light at a selected wavelength or range of wavelengths. The wavelengths can be any suitable wavelength, for example, visible spectrum light, infrared light, x-ray (e.g., for fluoroscopy), to name a few examples. In some embodiments, illumination sources 410 can include light-emitting diodes (LEDs) located at the distal end of the instrument 400. In some embodiments, illumination sources 410 can include one or more fiber optic fibers extending through a length of the endoscope to transmit light through the distal end from a remote light source, for example, an x-ray generator. Where the distal end includes multiple illumination sources 410 these can each be configured to emit the same or different wavelengths of light as one another.

The imaging device 415 can include any photosensitive substrate or structure configured to convert energy representing received light into electric signals, for example, a charge-coupled device (CCD) or complementary metal-oxide semiconductor (CMOS) image sensor. Some examples of imaging device 415 can include one or more optical fibers, for example, a fiber optic bundle, configured to transmit light representing an image from the distal end 400 of the endoscope to an eyepiece and/or image sensor near the proximal end of the endoscope. Imaging device 415 can additionally include one or more lenses and/or wavelength pass or cutoff filters as required for various optical designs. The light emitted from the illumination sources 410 allows the imaging device 415 to capture images of the interior of a patient's luminal network. These images can then be transmitted as individual frames or series of successive frames (e.g., a video) to a computer system such as command console 200.

Figure 22:
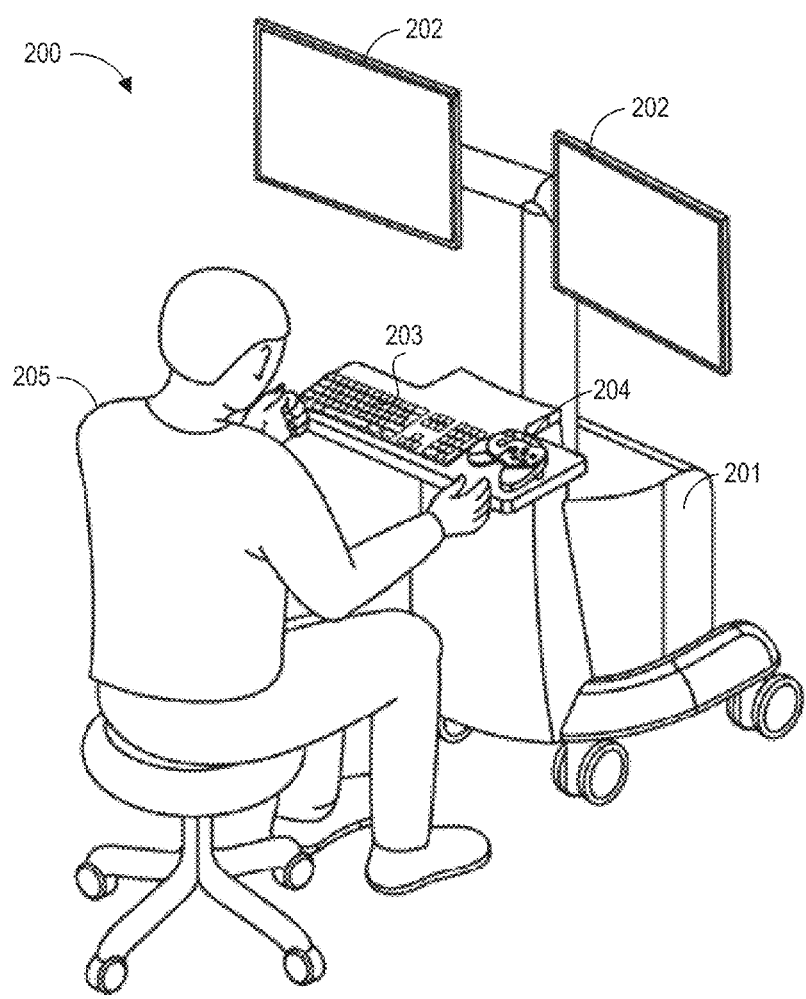
FIG. 22 illustrates an example command console, including a display, for an example medical robotic system, according to one embodiment.

FIG. 22 illustrates an example command console 200 that can be used with some implementations of the robotic systems described herein. As illustrated, in some embodiments, the command console 200 includes a console base 201, displays 202 (e.g., monitors), and one or more control modules (e.g., keyboard 203 and joystick 204). A user 205 (e.g., a physician) can remotely control the medical robotic system (e.g., the systems described with reference to FIGS. 1-15) from an ergonomic position using the command console 200. For example, the user 205 can use the command console 200 to navigate an instrument within a luminal network of the a patient. The command console 200 may also display information to the user 205 that can be used to aid in navigation of the luminal network.

The displays 202 may include electronic monitors (e.g., LCD displays, LED displays, touch-sensitive displays), virtual reality viewing devices (e.g., goggles or glasses), and/or other display devices. In some embodiments, one or more of the displays 202 can display the preoperative model 150 of the patient's luminal network 130. The displays 202 can also display image information received from a camera or another sensing device positioned on the instrument within the luminal network 130. In some embodiments, a model or representation of the instrument is displayed with the preoperative model 150 to help indicate a status of a surgical or medical procedure.

In some embodiments, the console base 201 includes a central processing unit (CPU or processor), a memory unit (computer-readable memory), a data bus, and associated data communication ports that are responsible for interpreting and processing signals such as camera imagery and tracking sensor data, e.g., from a medical instrument positioned within a luminal network of a patient. In some instances, the methods for navigation path tracing described below are executed by the processor of the console base 201. The console base 201 may also process commands and instructions provided by the user 205 through control modules 203, 204. In addition to the keyboard 203 and joystick 204 shown in FIG. 22, the control modules may include other devices, such as computer mice, trackpads, trackballs, control pads, controllers such as handheld remote controllers, and sensors (e.g., motion sensors or cameras) that capture hand gestures and finger gestures. A controller can include a set of user inputs (e.g., buttons, joysticks, directional pads, etc.) mapped to an operation of the instrument (e.g., articulation, driving, water irrigation, etc.). Using the control modules 203, 204 of the console base 200, the user 205 may navigate an instrument through the luminal network 130.

A. Example Navigation Path Tracing Methods and Systems.

Figure 23A:
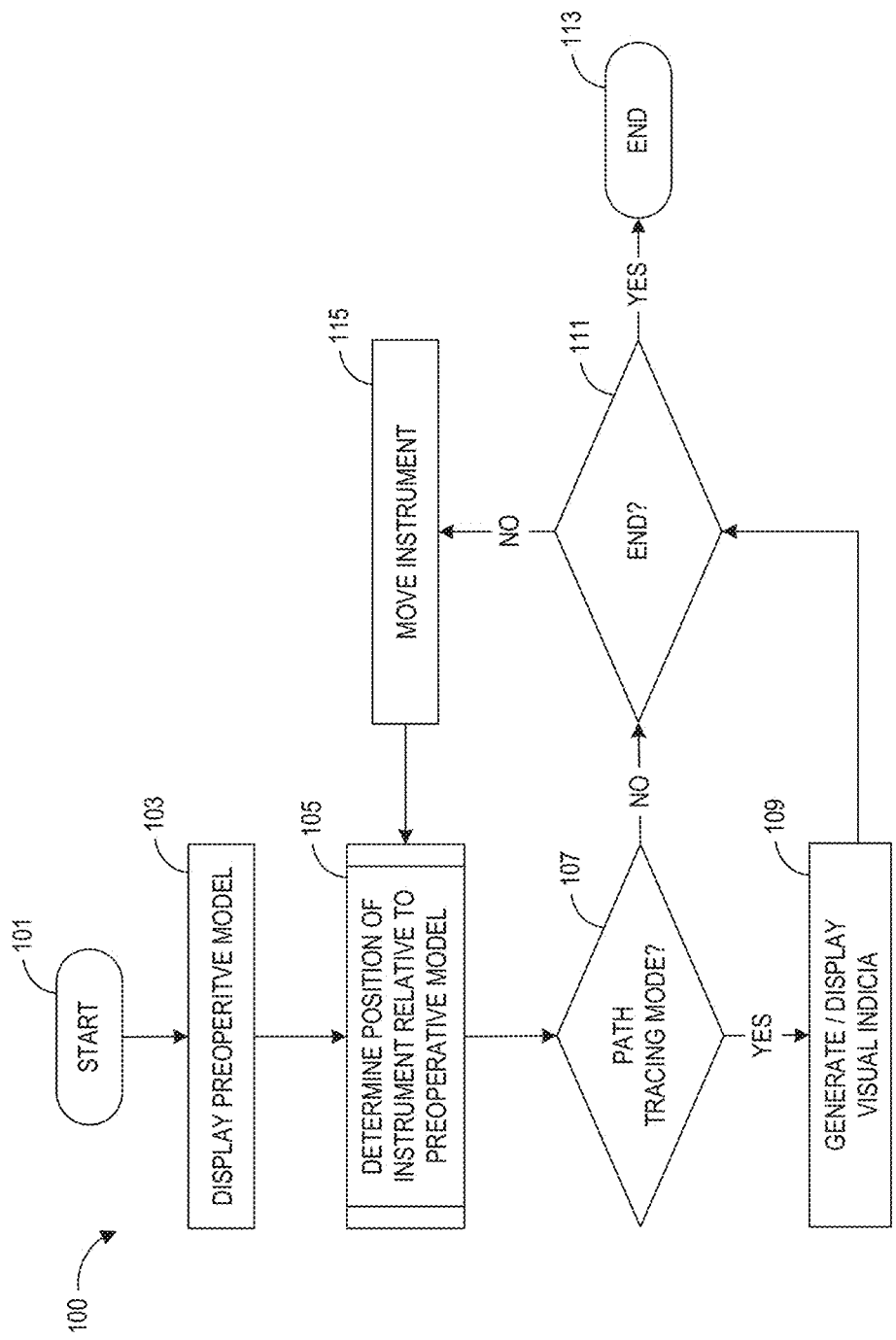
FIG. 23A is a flowchart illustrating an example navigation path tracing method that can be implemented in certain robotic systems.

FIG. 23A is a flowchart illustrating an example navigation path tracing process, algorithm, or method 100. The method 100 can be implemented in certain robotic systems, such as the robotic systems illustrated in FIGS. 1-15 and others. The method 100 can be implemented in or by a navigation system, such as the navigation or localization system 90 of FIG. 15. In some embodiments, one or more computer devices may be configured to execute the method 100. The computer devices may be embodied by a processor (or processors) and computer-readable memory in one or more components discussed above. The computer-readable memory may store instructions that may be executed by the processor(s) to perform the method 100. The instructions may include one or more software modules. By way of example and not limitation, the computer devices may be in the tower 30 shown in FIG. 1, the cart shown in FIGS. 1-4, the beds shown in FIGS. 5-10, the command console 200 shown in FIG. 22, etc.

The method 100 (or a system implanting the method 100) can be configured to provide (e.g., plot or otherwise display)

visual indicia (see, for example, FIGS. 25-27) indicative of positions (e.g., historical and/or current positions) of a medical instrument positioned within a luminal network (such as the luminal network 130 of FIG. 16). The visual indicia can represent a path traveled by the medical instrument as it navigates the luminal network. The visual indicia can be displayed to user, via a user display (such as display 202 of FIG. 22). The displayed visual indicia may provide a user with a visualization of one or more portions of the luminal network navigated by medical instrument. The visual indicia can also be used to extend a preoperative model of the luminal network. These and other features achieved in some implementations of the method 100 will be described in greater detail below.

The navigation path tracing method 100 beings at block 101. The method 100 may be executed, for example, as a medical instrument is navigated through a luminal network 130, for example, as shown in FIG. 21. The method 100 may thus be triggered, in some embodiments, when the medical instrument is introduced into the luminal network 130. In some embodiments, the method 100 may be triggered automatically. In some embodiments, the method 100 may be triggered manually, for example, when a user input or command is received. As mentioned above, the method 100 can be implemented for navigation of a wide variety of luminal networks, included branched luminal networks (such as bronchial networks, renal networks, cardiovascular networks (e.g., arteries and veins), etc.) and non-branched (e.g., single lumen) luminal networks (such as gastrointestinal tracts, urinary tracts, etc.).

At block 103, the method 100 displays a preoperative model (e.g., preoperative model 150), which may involve, e.g., displaying, on a user interface, a preoperative model corresponding to a mapped portion of a luminal network. As noted previously, the preoperative model 150 may be generated preoperatively (prior to the current procedures), using various imaging and mapping techniques. The preoperative model 150 can comprise a 3D model. The preoperative model 150 can be retrieved from a memory. the preoperative model 150 can be stored in a memory, for example, as preoperative model data 91 described with reference to FIG. 15. The preoperative model 150 can be representative of or correspond to at least a portion of the luminal network 130. Accordingly, in some embodiments, the preoperative model 150 can be representative of and correspond to a mapped portion 155 of the luminal network 130, as shown in FIG. 18. In some embodiments, an unmapped portion 135 (see FIG. 18) of the luminal network 130 may not be represented by the preoperative model 150. The preoperative model 150 can by displayed on a user display (e.g., user display 202). The user display may be part of the command console 200 or another device.

With the preoperative model 150 displayed, the method 100 moves to block 105. At block 105, the method 100 determines the position of the medical instrument relative to the preoperative model 150, which may involve, e.g., determining a position of a distal end of an instrument within the luminal network relative to the mapped portion of the luminal network. In some embodiments, position is determined or estimated using the navigation or localization system 90 described above and shown in FIG. 15. The localization system 90 may use various technologies or modalities, such as pre-operative mapping, computer vision, real-time EM tracking, and robot command data either individually or in combination to determine or estimate the position of the instrument. In some cases, radiation-based imaging modalities (e.g., fluoroscopy) may be used. In such cases, the radiation-based imaging modalities may be supplemented by pre-operative mapping, computer vision, real-time EM tracking, and/or robot command data.

As described above, the localization system 90 may include a localization module 95 that processes multiple types of input data 91-94 from various modalities to generate location data 96 for a medical instrument (for example, location date 96 may indicate a position of a distal tip of the instrument). The various types of input data can include, e.g., pre-operative model data 91 (e.g., preoperative model 150), vision data 92, EM data 93 (or other position sensor data), shape sensing data, and/or robotic command and kinematics data 94 as described above. Further, in some cases, localization system 90 may use a probabilistic approach that assigns a confidence weight to the location determined from each of the input data 91-94. Thus, where one type of data may not be reliable (for various reason) the confidence of the location determined by that type of data can be decrease and the localization module 95 may rely more heavily on another type of data in determining the position of the instrument.

The localization system 90 provides location data 96 indicative of the position of the instrument. The location data 96 can be presented in a coordinate frame that has been registered to the preoperative model 150, such that the position of the instrument relative to the preoperative model 150 can be determined. For example, the EM data 93 (or other position sensor data) can be registered to the preoperative model 150 as described above, such that the position determined by the EM data can be presented within the coordinate frame of the preoperative model 150. In some instances, one or more of the various other modalities (e.g., the vision data 92 and/or the robotic command and kinematics data 94) can also be registered to the coordinate frame of the model 150. In some implementations, the location data 96 can be displayed to the user 205 on one of the displays 202.

Additionally, in some embodiments, certain of the localization modalities may be utilized only when the instrument is positioned within a portion of the luminal network 130 that is mapped by the preoperative model 150. For example, in some embodiments, the vision data 92 can be used to determine a position estimate for the instrument only when the instrument is positioned within the preoperative model 150. This may be because, in some embodiments, determining position based on the vision data 92 also relies partially on the preoperative model data 91. For example, vision data 92 may be compared to preoperative model data 91 to determine position. Outside the preoperative model 150, vision data 92 may provide an unreliable estimate of position in some embodiments. Similarly, in some embodiments, the robotic command and kinematics data 94 can be used to determine a position estimate for the instrument only when the instrument is positioned within the preoperative model 150. This may be because, in some embodiments, determining positon based on the robotic command and kinematics data 94 also relies partially on the preoperative model data 91. For example, robotic command and kinematics data 94 may be in conjunction with preoperative model data 91 to determine position. Outside the preoperative model 150, robotic command and kinematics data 94 may provide an unreliable estimate of position in some embodiments.

In contrast, in some embodiments, certain of the localization modalities may be utilized regardless of whether the instrument is positioned within a portion of the luminal network 130 that is mapped by the preoperative model 150. For example, in some embodiments, EM data 93 (or other position sensor data) may be used to determine position regardless of whether the instrument is positioned within a portion of the luminal network 130 that is mapped by the preoperative model 150. This may be because, apart from being registered to the coordinate frame of the preoperative model 150, the location determination of EM data 93 (or other position sensor data) may be independent of the preoperative model data 91.

As another example, in some embodiments, vision data 92 and robot and robotic command and kinematics data 94 may provide a navigation modality that is not dependent on whether the instrument is positioned within the preoperative model 150. For example, a vision algorithm or module may analyze images received from the imaging device 415 on the instrument to detect one openings to lumens. A robotic command and kinematics algorithm or module can analyze movement of the instrument through the lumen to estimate travel length of the instrument. These modalities can be combined to develop a position estimate that is not based on the preoperative model 150. In some instances, vision data 92 and robot and robotic command and kinematics data 94 is combined to develop an artificial or two-dimensional estimate of the instrument position.

In some embodiments, other modalities are used to determine position (within a coordinate frame that has been registered to the preoperative model) without further basis on the preoperative model 150 and/or preoperative model data 91. These can include fluoroscopy, shape sensing fibers, position and/or motion sensors, etc.

In some embodiments, at block 105, the method 100 determines whether the instrument is positioned inside or outside a portion of the luminal network 130 that is represented by the preoperative model 150. In some embodiments, if the instrument is positioned within a portion of the luminal network 130 that is represented by the preoperative model 150, the location is determined relative to the preoperative model 150 (e.g., in a coordinate frame that has been mapped to the preoperative model 150) using modalities that are dependent on preoperative model data 91 and/or modalities that are not dependent on preoperative model data 91. In some embodiments, if the instrument is positioned outside a portion of the luminal network 130 that is represented by the preoperative model 150, the location is determined relative to the preoperative model 150 (e.g., in a coordinate frame that has been mapped to the preoperative model 150) using modalities that are not dependent on preoperative model data 91. In some embodiments, modalities that are not dependent on preoperative model data 91 include EM data 93 and/or other position sensor data that has been registered to the coordinate frame of the preoperative model 150.

After determining the position of the instrument relative to the preoperative model at block 105, the method 100 moves to decision state 107. At decision state 107, the method 100 determines whether to enter or remain in path tracing mode, which may involve, e.g., determining when the distal end of the instrument has been advanced past the mapped portion of the luminal network into an unmapped portion of the luminal network and entering a path tracing mode. As will be described in greater detail below, with reference to FIGS. 25-27, in path tracing mode, visual indicia can be displayed to indicate a historical path of the instrument through the luminal network 130.

In some examples, the determination of whether to enter or remain in path tracing mode is made based at least in part on the position of the instrument relative to the preoperative model 150 determined at block 105. For example, the method 100 may enter or remain in path tracing mode when the instrument is positioned outside of the preoperative model 150. Thus, in some embodiments, the method 100 triggers path tracing mode when the instrument is outside of the mapped portion 155 of the luminal network 130 as represented by the preoperative model 150.

As another example, the determination of decision state 107 can be made based on proximity to an end of the preoperative model 150 or an end of a segment of the preoperative model 150. For example, the method 100 may enter path tracing mode when the instrument is positioned within 0.1 mm, 0.25 mm, 0.5 mm, 0.75 mm, 1 cm, 1.5 cm, 2 cm, 2.5 cm, 3 cm, 4 cm, 5 cm, 7.5 cm, or 10 cm of and end of the preoperative model 150 or an end of a segment of the preoperative model 150. As another example, the method 100 may enter path tracing mode when the instrument is positioned within 1%, 2.5%, 5%, 7.5%, 10%, 15%, 20%, 25%, or 50% of the a length of the preoperative model 105 or the length of a segment (such as a last segment) of the preoperative model 150. Thus, in some instances, path tracing mode is triggered before the instrument is moved beyond the preoperative model 150. Alternatively or additionally, in some implementations, path tracing mode is activated when the instrument is positioned within the preoperative model 150.

As another example, the determination of decision state 107 can be made based on a direction of travel of the instrument within the luminal network 130. For example, in some instances, path tracing mode is activated when the instrument is advanced into the luminal network 130, retracted backwards in the luminal network 130, or both.

As another example, the determination of decision state 107 can be made based on a distance traveled by the instrument within the luminal network 130. For example, in some instances, path tracing mode is activated when the instrument has traveled at least 0.1 mm, 0.25 mm, 0.5 mm, 0.75 mm, 1 cm, 1.5 cm, 2 cm, 2.5 cm, 3 cm, 4 cm, 5 cm, 7.5 cm, or 10 cm. Other distances can also be used.

As another example, the determination of decision state 107 can be made based on time elapsed. For example, path tracing mode can be activated every 0.1 seconds, 0.25 seconds, 0.5 seconds, 0.75 seconds, 1 second, 1.5 seconds, 2 seconds, 2.5 seconds, 3 seconds, 4 seconds, 5 seconds, 7.5 seconds, or 10 seconds. Other periods of time can also be used.

In some examples, the determination of whether to enter or remain in path tracing mode is made based at least in part on user input. For example, in some instances, a user may activate or deactivate path tracing mode as desired. In some embodiments, this is accomplished by entering a user command at the command console 200.

Other factors may also be considered for determining whether to enter or remain in path tracing mode. Further, in some instances, a combination factors may be considered at decision state 107.

If decision state 107 determines to enter or remain in path tracing mode, the method 100 moves to block 109, at which visual indicia are generated and/or displayed, which may involve, e.g. displaying visual indicia of a path of the distal end of the instrument in the unmapped portion of the luminal network relative to the preoperative model of the mapped portion of the luminal network. As noted previously, the visual indicia are indicators of the historical position of the instrument as it travels through the luminal network 130. The visual indicia can create a trail (e.g., breadcrumbs or a historical path) that represents the path of travel of the instrument through the luminal network 130. The visual indicia can be displayed on display 202. The visual indicia can comprise many types of indicators as described with reference to FIGS. 25-27 below.

After visual indicia are generated and displayed at block 109, the method 100 moves to decision state 111. At decision state 111, the method determines whether to end (for example, if a procedure is finished) or to continue (for example, if a procedure will continue). If decision state 111 determines that the method 100 should end, the method ends at block 113. If decision state 111 determines that the method 100 will continue the method moves to block 115.

At block 115, the instrument is moved to a new position within the luminal network 130. This may be accomplished by or advancing or retracting the instrument within the luminal network 130. This may be accomplished by articulating the instrument. The method 100 then returns to block 105, at which the new position of the instrument within the luminal network 130 is determined.

As shown in FIG. 23A, while the method 100 continues, the method 100 includes two possible loops for each new position after the instrument is moved within the luminal network. If decision state 107 determines that path tracing mode is active, the loop generates and displays a new visual indicia for the new position. If the decision state 107 determines that path tracing mode is inactive, no new visual indicia is generated or displayed. Thus, the criteria used by decision state 107 can be varied to determine when to display visual indicia. As noted above, these criteria can include whether the instrument is inside or outside the preoperative model, distance traveled by the instrument (e.g., since the previous visual indicia), direction of travel, time elapsed between previous visual indicia, etc. One of skill in the art will appreciate that these criteria can be varied to determine the frequency with which visual indicia are generated as well as the a distance between successive visual indicia.

The path tracing method 100 (or system implementing the same), thus can generate and display visual indicia indicative of historical positions of the instrument as the instrument travels through a luminal network. As visual indicia are generated and displayed, lumens traveled by the instrument can be visualized. Data regarding the lumens traveled can be associated with visual indicia and displayed to the user. The data and visual indicia can also be stored for future use. In some instances, tube-like structures can be fitted around the visual indicia to extend the preoperative model into portions of the luminal network that were previously unmapped by the preoperative model. The path tracing method 100 (or system implementing the same) can thus advantageously aid a user in navigation and visualizing the luminal network.

Figure 23B:
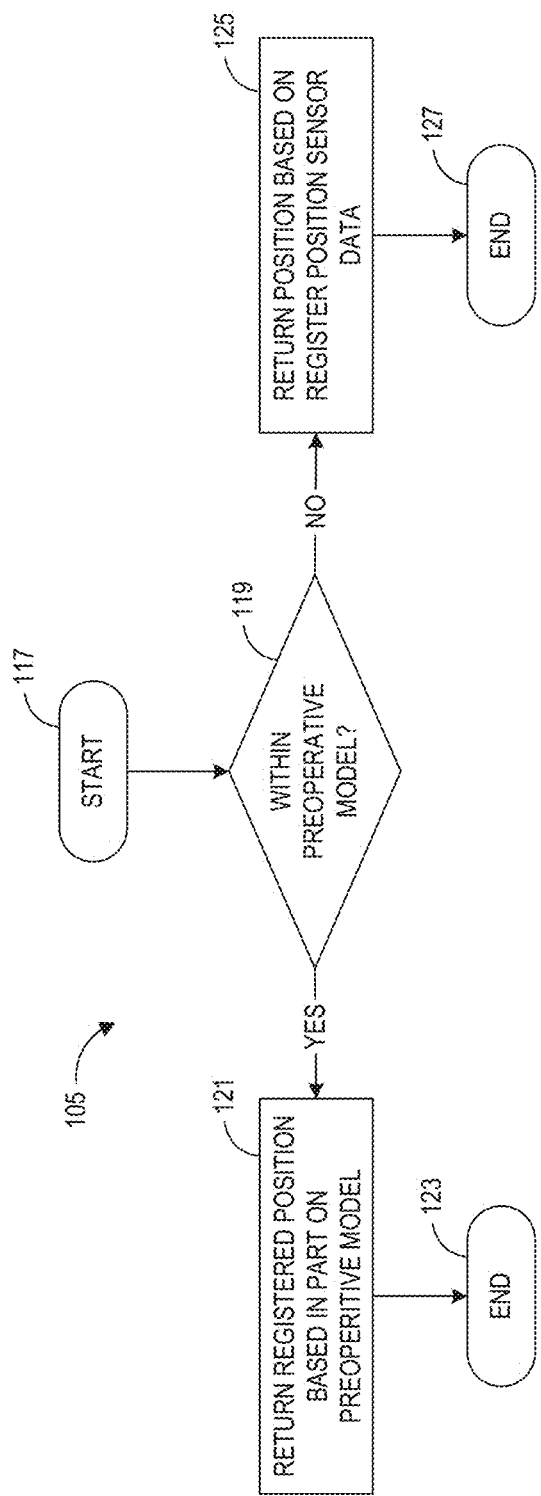
FIG. 23B is a flowchart illustrating an example method of determining position of an instrument within a luminal network as part of certain navigation path tracing methods.

FIG. 23B is a flowchart illustrating an example subroutine for, in some embodiments, performing step 105 of the method 100 of FIG. 23A. The subroutine of FIG. 23B need not be included in all implementations of method 100. The subroutine provides a method of determining the position of the instrument within the luminal network 130. The subroutine begins at block 117. At decision state 119, the subroutine determines whether the instrument is positioned within the preoperative model 150. For example, after registering the location data 96 to a coordinate frame of the preoperative model, the location data 96 can be compared to the preoperative model 150 to determine whether the instrument is within the mapped portion 155 or the unmapped portion 135 of the luminal network 130 (see FIG. 18).

If the instrument is determined to be within the preoperative model 150, the subroutine moves to block 121. At block 121, the subroutine returns a position (e.g., position data 96) that is based in part on the preoperative model 150 and/or preoperative model data 91. That is, when the instrument is positioned within the preoperative model 150, the subroutine can return position data that is based at least in part on navigation modalities that make use of the preoperative model 150 and/or the preoperative model data. The subroutine then ends at block 123.

If at decision state 119 the instrument is determined to be outside of the preoperative model 150, the subroutine moves to block 125. At block 125, the subroutine returns a position that, apart from being registered to the coordinate frame of the preoperative model 150, is not based on the preoperative model 150 and/or preoperative model data 91. That is, when the instrument is positioned outside the preoperative model 150, the subroutine can return position data that is based on navigation modalities that do not make use of the preoperative model 150 and/or the preoperative model data (apart from having their output registered to the coordinate frame of the preoperative model 150). This may be because the instrument may be positioned outside of the preoperative model and data from navigation modalities that rely on the preoperative model 150 or preoperative model date 91 may be unavailable. The subroutine then ends at block 127.

Considering decision state 119, the subroutine returns a position based on various navigation modalities depending on whether the instrument is within the preoperative model 150. When the instrument is within the preoperative model 150, a greater number of navigation modalities may be available to the localization system 90 than when the instrument is outside of the preoperative model 150.

In some embodiments, EM data 93 (or other position sensor data) may provide a navigation modality that is not dependent on whether the instrument is positioned within the preoperative model 150. That is, apart from being registered to the coordinate frame of the preoperative model 150, the EM data 93 (or other position sensor data) may provide a location determination that is not based on the preoperative model 150. Thus, EM data 93 may be used to return position without basis on the preoperative model at block 125 of the subroutine.

Figure 24:
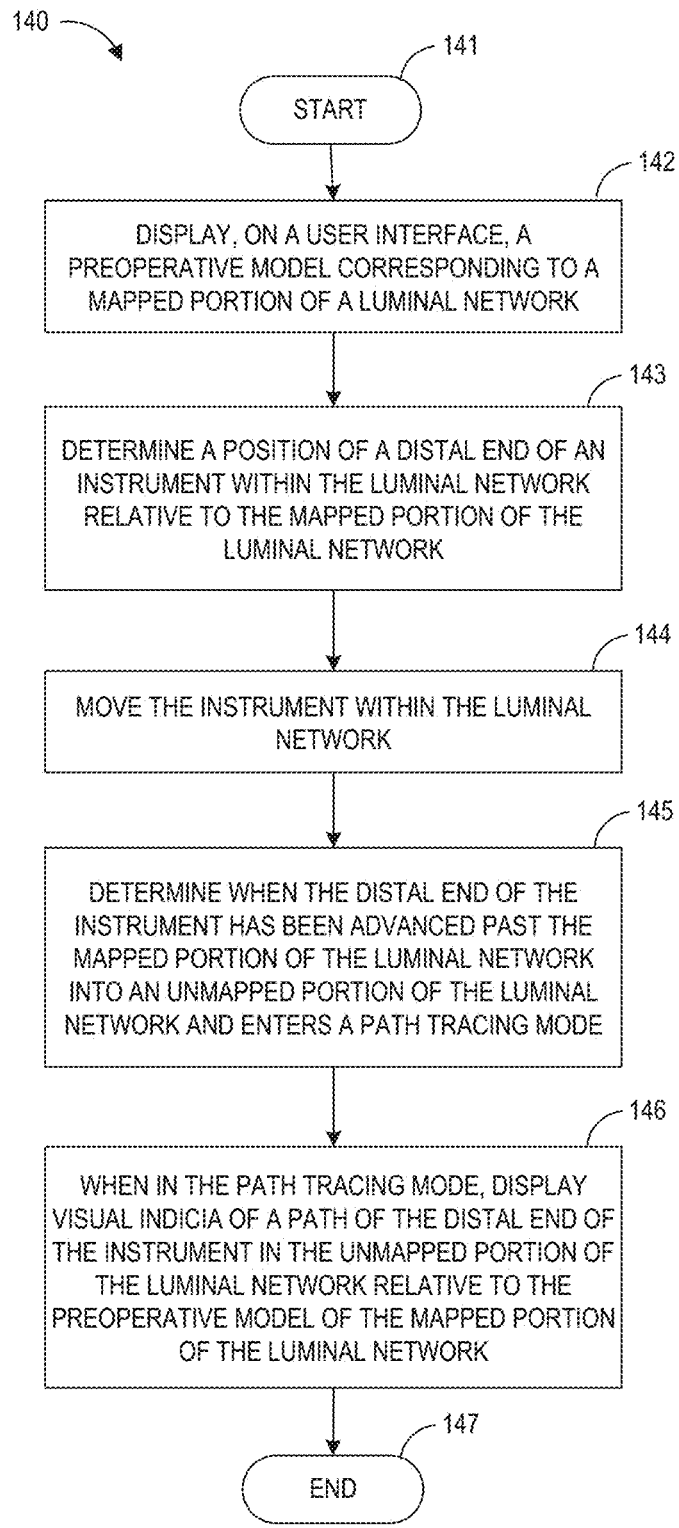
FIG. 24 is a flowchart illustrating an example method of determining a navigation path of an instrument within a luminal network.

FIG. 24 is a flowchart illustrating an example process, algorithm, or method 140 of determining a navigation path of an instrument within a luminal network. As with the method 100 of FIG. 23A, the method 140 of FIG. 24 can be implemented in certain robotic systems, such as the robotic systems illustrated in FIGS. 1-15 and others. The method 140 can be implemented in or by a navigation system, such as the navigation or localization system 90 of FIG. 15.

The method 140 beings at block 141. At block 142, the method 100 displays, on a user interface, a preoperative model corresponding to a mapped portion of a luminal network. As noted above with reference to the method 100 of FIG. 23A, the preoperative model 150 may be generated preoperatively (prior to the current procedures), using various imaging and mapping techniques. Numerous aspects described above with reference to the method 100 of FIG. 23A are applicable to the method 140 of FIG. 24, and will not be repeated for the sake of brevity.

At block 143, the method 140 determines a position of a distal end of an instrument within the luminal network relative to the mapped portion of the luminal network. In some embodiments, position is determined using the navigation or localization system 90 described above and shown in FIG. 15. The localization system 90 may use various technologies or modalities, such as, e.g., pre-operative mapping, computer vision, real-time EM tracking, shape sensing fiber data, and/or robot command and kinematics data to determine or estimate the position of the instrument.

At block 144, the method 140 moves the instrument within the luminal network. This may be accomplished by or advancing or retracting the instrument within the luminal network 130. This may be accomplished by articulating the instrument.

At block 145, the method 140 determines when the distal end of the instrument has been advanced past the mapped portion of the luminal network into an unmapped portion of the luminal network and enters a path tracing mode. In path tracing mode, visual indicia can be displayed to indicate a historical path of the instrument through the luminal network 130.

At block 146, the method 140, when in the path tracing mode, displays visual indicia of a path of the distal end of the instrument in the unmapped portion of the luminal network relative to the preoperative model of the mapped portion of the luminal network. The visual indicia can comprise many types of indicators as described with reference to FIGS. 25-27 below. The method 140 ends at block 147.

C. Example Navigation Path Tracing Outputs and Displays.

Figure 25:
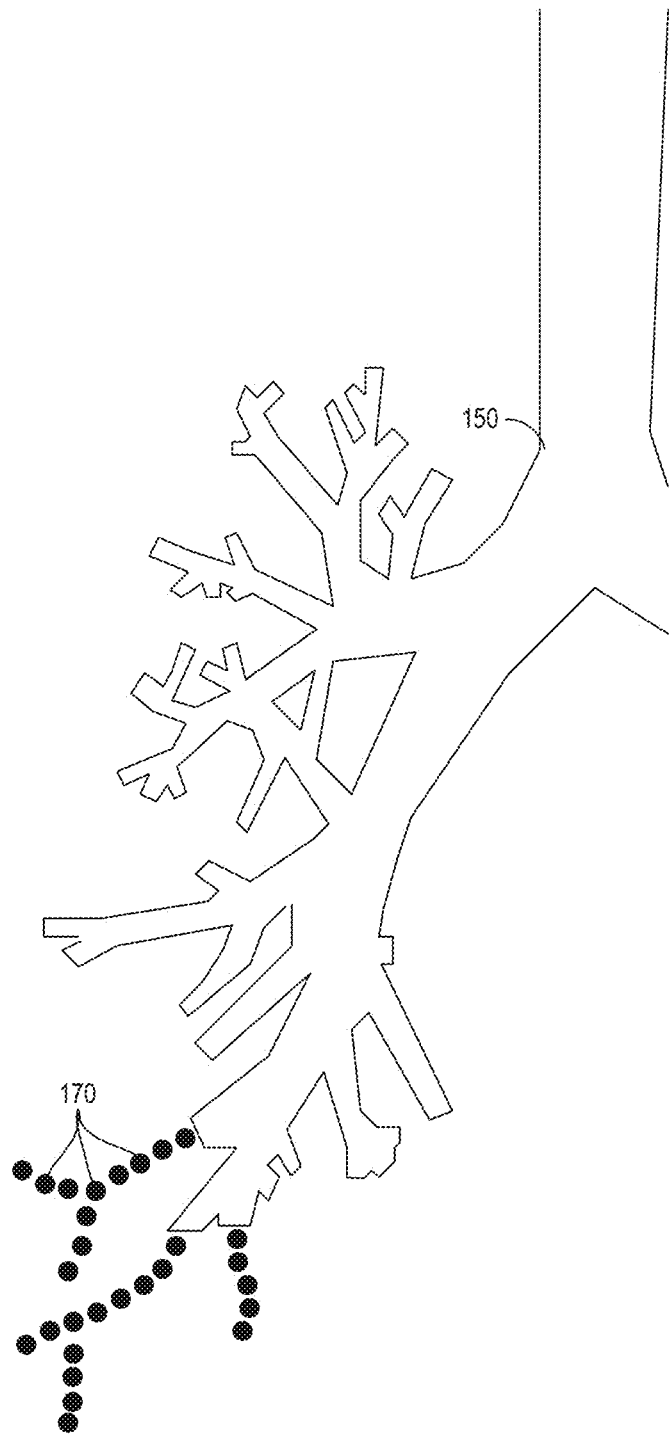
FIG. 25 provides an example output of a navigation path tracing system.

FIG. 25 provides an example output of a navigation path tracing system or method illustrating visual indicia 170. In the illustrated example, the visual indicia 170 are illustrated as circles, but this need not be the case in all embodiments. For example, the visual indicia 170 can be any suitable shape or marker, such as dots, dashes, X's, other shapes, etc. As shown in FIG. 25, the visual indicia 170 can reveal the shape of portions of the luminal network 130 that are not represented by the preoperative model 150. That is, as the instrument is moved through the luminal network 130 and visual indicia 170 are plotted or displayed (for example, when in path tracing mode), the visual indicia 170 can provide an indication of the shape or structure of the luminal network 130.

Figure 26:
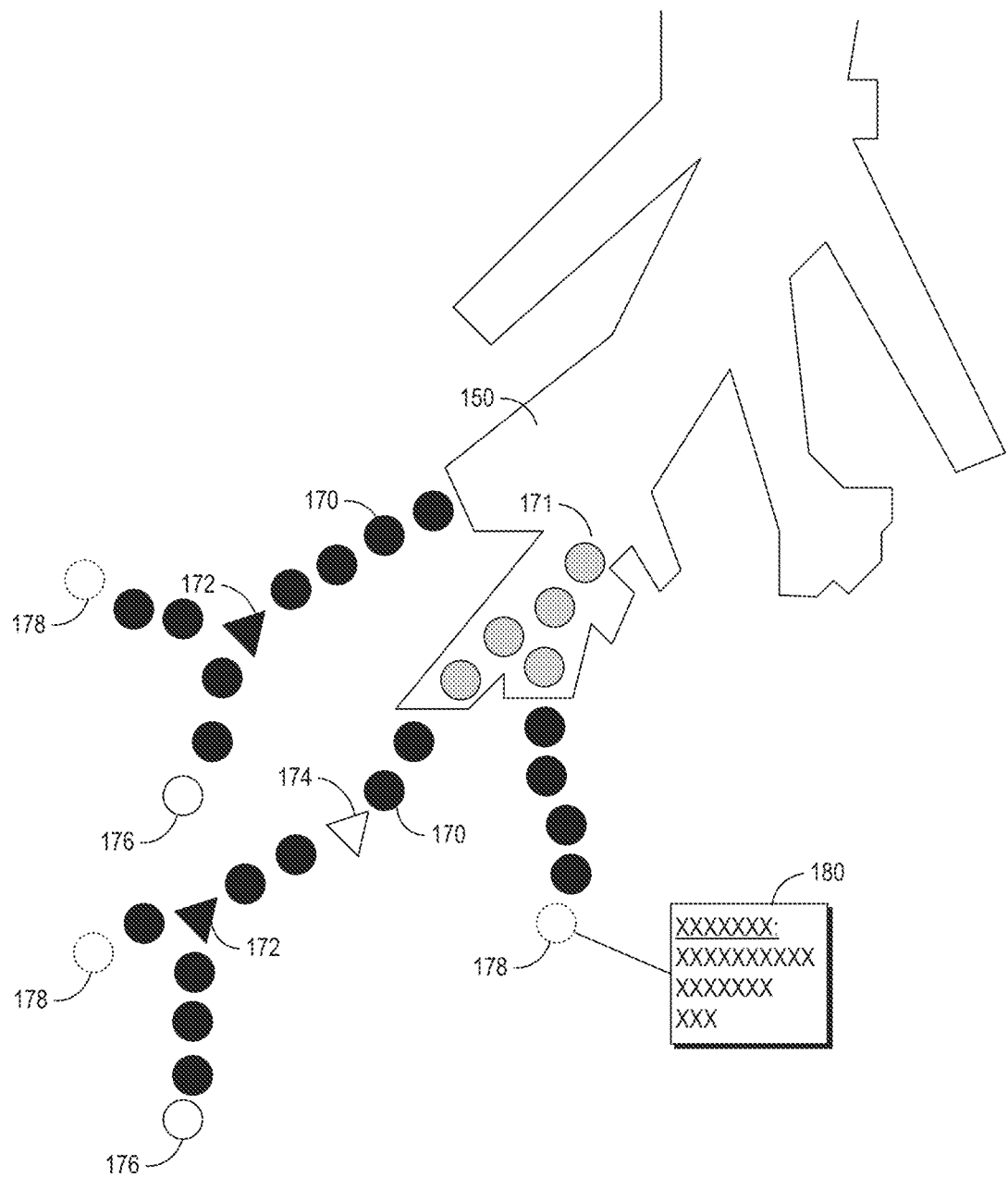
FIG. 26 provides another example output of a navigation path tracing system.

FIG. 26 provides another example output of a navigation path tracing system or method, illustrating several different types of visual indicia. The visual indicia can vary to provide various types of information to a user. For example, in the illustrated example of FIG. 26, visual indicia 170 are illustrated as darkened circles. Visual indicia 170 can represent a position of the instrument within a lumen of the luminal network. Visual indicia 172, 174 are illustrated as triangles. Visual indicia 172, 174 can represent positions of the instrument within the luminal network 130 at which branches are present. Visual indicia 172 is illustrated as a darkened triangle, which can signify that the instrument has traveled down all available branches at that location. Visual indicia 174 is illustrated as an undarkened triangle, which can signify that a branch from that location has not yet been explored by the instrument. Visual indicia 176, 178 are illustrated as undarkened circles. In this example, undarkened circles can represent the farthest points within lumens that the instrument has explored. Visual indicia 176 is illustrated as an undarkened circle with a solid outline. This can represent a position an end of a lumen, or a point at which the instrument cannot proceed further into the lumen because of, for example, the relative size of the instrument and the lumen. Visual indicia 178 is illustrated as an undarkened circle with a dashed outline. This can represent that the lumen continues and has not yet been explored by the instrument. Visual indicia 171 are illustrated as gray circles. In the illustrated example, visual indicia 171 illustrate historical positions of the instrument within the preoperative model.

The various visual indicia illustrated in FIG. 26 are provided by way of example only and are not intended to be limiting. These examples illustrate that various types of visual indicia can be used to provide different information to a user regarding the historical positions of the instrument as well as various information about the luminal network 130. The specific symbols used to illustrate the various visual indicia, as well as the type of information that can be represented, can be widely varied.

In some instances, visual indicia may vary over time. For example, visual indicia may fade over time such that more recently traveled portions are darker than previously traveled portions.

As shown in FIG. 26, in some implementations, data 180 can be associated with the visual indicia. For example, a user (e.g., a physician) can create a note containing data associated with certain visual indicia. The user may enter the data 180 via the command console 200 and the data 180 can be viewed via the displays 202.

Additionally, the method 100 (or a system implementing the method 100) can associate various other types of data with the visual indicia. For example, vision data (e.g., an image of the lumen at the location represented by the visual indicia) can be associated with the visual indicia. Various information can be derived from the vision data such as whether branches are present, diameter/size of the lumen, etc.

Figure 27:
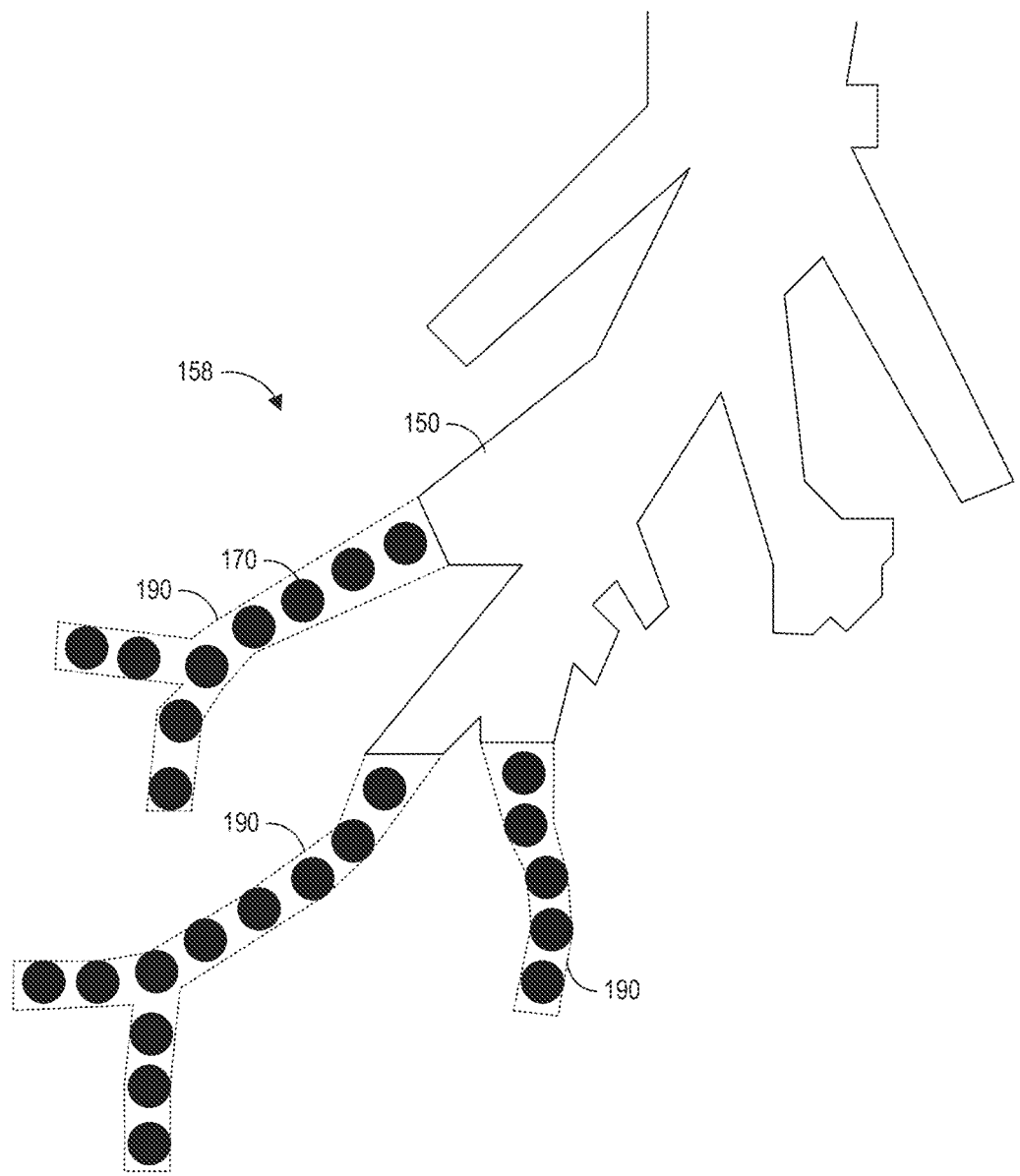
FIG. 27 provides another example output of a navigation path tracing system and illustrates that the navigation path tracing system can be used to extend the preoperative model.

FIG. 27 provides another example output of a navigation path tracing system or method and illustrates that the navigation path tracing system can be used to extend the preoperative model 150. As shown in FIG. 27, visual indicia 170 can be grouped to extend the preoperative model 150. For example, path tracing mode can identify strings of visual indicia 170 as corresponding to a lumen and fit a tube-like structure 190 to the string of visual indicia to extend the preoperative model 190. The diameter of the tube-like structure 190 can be determined using vision data of the interior of the lumen or other methods. Thus, the tube-like structures 190 extend the preoperative model 150 into portions of the luminal network 130 that were previously unmapped by the preoperative model 150. The extending preoperative model can be saved, for example, in a computer-readable memory, for use during future procedures.

3. Implementing Systems and Terminology

Implementations disclosed herein provide systems, methods and apparatuses for navigation path tracing. Various implementations described herein provide for improved navigation of luminal networks.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The position estimation and robotic motion actuation functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the term "approximately" refers to a range of measurements of a length, thickness, a quantity, time period, or other measurable value. Such range of measurements encompasses variations of +/−10% or less, preferably +/−5% or less, more preferably +/−1% or less, and still more preferably +/−0.1% or less, of and from the specified value, in so far as such variations are appropriate in order to function in the disclosed devices, systems, and techniques.

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A non-transitory computer readable storage medium having stored thereon instructions that, when executed, cause a processor of a device to at least:
    display, on a user display, a preoperative model corresponding to a mapped portion of a luminal network of a patient;
    determine a position of a distal end of an instrument that is configured to be positioned within the luminal network relative to the mapped portion of the preoperative model;
    determine that the position of the distal end of the instrument is within a predetermined distance of a boundary corresponding to a transition from an end of the mapped portion of the preoperative model to a portion of the luminal network that is unmapped in the preoperative model prior to the distal end of the instrument reaching the boundary;
    enter a path tracing mode in response to determining that the position of the distal end of the instrument is within the predetermined distance of the boundary prior to the distal end of the instrument reaching the boundary; and
    when in the path tracing mode, display, on the user display, visual indicia indicative of a path traversed by the distal end of the instrument with respect to the displayed preoperative model as the instrument is navigated through the luminal network.

2. The non-transitory computer readable storage medium of claim 1, wherein the instructions are configured to cause the processor of the device to deactivate the path tracing mode when the position of the distal end of the instrument returns to the mapped portion of the preoperative model from the unmapped portion of the preoperative model.

3. The non-transitory computer readable storage medium of claim 1, wherein the instructions are configured to cause the processor of the device to enter the path tracing mode when the position of the distal end of the instrument is within 25%, 20%, 15%, 10%, or 5% an end of a last segment of the preoperative model.

4. The non-transitory computer readable storage medium of claim 1, wherein the visual indicia are indicative of historical positions of the distal end of the instrument within the luminal network.

5. The non-transitory computer readable storage medium of claim 1, wherein, in path tracing mode, the instructions are configured to cause the processor of the device to adjust a frequency of the visual indicia based on a distance traveled by the instrument between the visual indicia.

6. The non-transitory computer readable storage medium of claim 1, wherein, in path tracing mode, the instructions are configured to cause the processor of the device to adjust a frequency of the visual indicia based on a time elapsed between the visual indicia.

7. The non-transitory computer readable storage medium of claim 1, wherein the instructions are configured to cause the processor of the device to determine the position of the distal end of the instrument based on a plurality of navigation modalities when the instrument is positioned within the mapped portion of the preoperative model, wherein the plurality of navigation modalities comprise a plurality of preoperative model data, vision data, position sensor data, and robotic command and kinematics data.

8. The non-transitory computer readable storage medium of claim 7, wherein the instructions are configured to cause the processor of the device to determine the position of the distal end of the instrument based on less than the plurality of navigation modalities when the instrument is positioned outside the mapped portion of the preoperative model.

9. The non-transitory computer readable storage medium of claim 1, wherein the instructions are configured to cause the processor of the device to associate vision data with the visual indicia, wherein the vision data comprises an image received from an imaging device on the distal end of the instrument.

10. The non-transitory computer readable storage medium of claim 1, wherein the instructions are configured to cause the processor of the device to associate robotic command and kinematics data with the visual indicia.

11. The non-transitory computer readable storage medium of claim 1, wherein the instructions are configured to cause the processor of the device to:
receive user input data from a user input; and
associate the user input data with the visual indicia;
wherein the user input data comprises one or more of:
an indication of a lumen traveled;
an indication of a lumen not traveled;
an indication of an end of a lumen;
an indication of an opening of a lumen;
an indication that a current lumen extends beyond a current position of the instrument; and
a lumen diameter.

12. The non-transitory computer readable storage medium of claim 1, wherein the instructions are configured to cause the processor of the device to:
detect when the position of the distal end of the instrument is moved into the mapped portion of the luminal network; and
stop displaying the visual indicia when the distal end of the instrument is positioned inside the mapped portion of the luminal network.

13. The non-transitory computer readable storage medium of claim 1, wherein the instructions are configured to cause the processor of the device to determine the position of the distal end of the instrument based on a plurality of navigation modalities when the instrument is positioned within the mapped portion of the preoperative model.

14. The non-transitory computer readable storage medium of claim 13, wherein the plurality of navigation modalities comprise a plurality of preoperative model data, vision data, position sensor data, and robotic command and kinematics data.

15. The non-transitory computer readable storage medium of claim 13, wherein the instructions are configured to cause the processor of the device to determine the position of the distal end of the instrument based on less than the plurality of navigation modalities when the instrument is positioned outside the mapped portion of the preoperative model.

16. The non-transitory computer readable storage medium of claim 1, wherein the instructions are configured to cause the processor of the device to determine the position of the distal end of the instrument based on EM data received from an EM sensor when the instrument is positioned outside the mapped portion of the preoperative model.

17. The non-transitory computer readable storage medium of claim 1, wherein the instructions are configured to cause the processor of the device to determine the position of the distal end of the instrument based on a combination of vision data and robotic command and kinematics data when the instrument is positioned outside the mapped portion of the preoperative model.

18. The non-transitory computer readable storage medium of claim 1, wherein the visual indicia comprise:
a first type of visual indicia indicative of a first historical position of the distal end of the instrument within the luminal network at which a first branch is present in the luminal network, the first type of visual indicia further indicating that the distal end of the instrument has traveled down all available child segments of the first branch, and
a second type of visual indicia indicative of a second historical position of the distal end of the instrument within the luminal network at which a second branch is present in the luminal network, the second type of visual indicia further indicating that the distal end of the instrument has not traveled down all available child segments of the second branch.

19. A robotic system for navigating a luminal network, the system comprising:
an instrument having an elongate body and a sensor disposed on a distal end of the elongate body;
at least one computer-readable memory having stored thereon executable instructions; and
one or more processors in communication with the at least one computer-readable memory and configured to execute the instructions to cause the one or more processors to at least:
access a preoperative model of a mapped portion of the luminal network and display the preoperative model on a user display;
determine a position of the distal end of the instrument within the luminal network relative to the preoperative model using the sensor;
determine that the position of the distal end of the instrument is within a predetermined distance of a boundary corresponding to a transition from an end of the mapped portion of the preoperative model to a portion of the luminal network that is unmapped in the preoperative model prior to the distal end of the instrument reaching the boundary;
enter a path tracing mode in response to determining that the position of the distal end of the instrument is within the predetermined distance of the boundary prior to the distal end of the instrument reaching the boundary; and
when in the path tracing mode, display visual indicia of a path traversed by the distal end of the instrument with respect to the displayed preoperative model on the user display as the instrument is navigated through the luminal network.

20. The system of claim 19, wherein the one or more processors are configured to execute the instructions to cause the one or more processors to register a coordinate frame of the sensor and a coordinate frame of the preoperative model.

21. The system of claim 19, the system further comprising a field generator configured to generate an EM field, wherein the sensor is an EM sensor, and wherein the one or more processors are configured to execute the instructions to cause the one or more processors to determine a position of the EM sensor within the EM field.

22. The system of claim 19, wherein the sensor is a shape sensing fiber.

23. The system of claim 19, wherein the one or more processors are configured to execute the instructions to cause the system to move the instrument within the luminal network.

24. The system of claim 19, wherein the one or more processors are configured to execute the instructions to cause the one or more processors to at least:
detect when the position of the distal end of the instrument is moved into the mapped portion of the luminal network; and
stop displaying the visual indicia when the distal end of the instrument is positioned inside the mapped portion of the luminal network.

25. A method of determining a navigation path of an instrument within a luminal network, the method comprising:
displaying, on a user interface, a preoperative model corresponding to a mapped portion of a luminal network;

determining a position of a distal end of an instrument within the luminal network relative to the mapped portion of the luminal network;

moving the instrument within the luminal network;

determining that the position of the distal end of the instrument is within a predetermined distance of a boundary corresponding to a transition from an end of the mapped portion of the preoperative model to a portion of the luminal network that is unmapped in the preoperative model prior to the distal end of the instrument reaching the boundary;

entering a path tracing mode in response to determining that the position of the distal end of the instrument is within the predetermined distance of the boundary prior to the distal end of the instrument reaching the boundary; and when in the path tracing mode, displaying visual indicia of a path traversed by the distal end of the instrument in the portion of the luminal network that is unmapped in the preoperative model relative to the preoperative model of the mapped portion of the luminal network as the instrument is navigated through the luminal network.

26. The method of claim 25, further comprising:

detecting when the position of the distal end of the instrument is moved into the mapped portion of the luminal network; and stopping displaying the visual indicia when the distal end of the instrument is positioned inside the mapped portion of the luminal network.

27. The method of claim 25, further comprising adjusting a frequency of the visual indicia based on a distance traveled by the instrument between the visual indicia.

28. The method of claim 25, further comprising adjusting a frequency of the visual indicia based on a time elapsed between the visual indicia.

29. The method of claim 25, further comprising associating vision data with the visual indicia, wherein the vision data comprises an image received from an imaging device on the distal end of the instrument.

* * * * *